US009974802B2

(12) United States Patent
Zomer et al.

(10) Patent No.: US 9,974,802 B2
(45) Date of Patent: *May 22, 2018

(54) COMPOSITION OF NOVEL CARBOHYDRATE DRUG FOR TREATMENT OF HUMAN DISEASES

(71) Applicant: Galectin Therapeutics, Inc., Norcross, GA (US)

(72) Inventors: Eliezer Zomer, Newton, MA (US); Peter G. Traber, Duluth, GA (US); Anatole A. Klyosov, Newton, MA (US); Elena Chekhova, Cambridge, MA (US)

(73) Assignee: Galectin Therapeutics, Inc., Norcross, GA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/478,599

(22) Filed: Apr. 4, 2017

(65) Prior Publication Data

US 2017/0202870 A1 Jul. 20, 2017

Related U.S. Application Data

(63) Continuation of application No. 14/575,062, filed on Dec. 18, 2014, which is a continuation of application No. 14/456,644, filed on Aug. 11, 2014, now Pat. No. 8,962,824, which is a continuation of application No. 13/573,442, filed on Sep. 14, 2012, now Pat. No. 8,871,925.

(60) Provisional application No. 61/580,830, filed on Dec. 28, 2011.

(51) Int. Cl.
| C08B 37/00 | (2006.01) |
| C08B 37/06 | (2006.01) |
| A61K 31/715 | (2006.01) |
| A61K 31/732 | (2006.01) |
| A61K 45/06 | (2006.01) |
| A61K 31/738 | (2006.01) |

(52) U.S. Cl.
CPC .......... *A61K 31/715* (2013.01); *A61K 31/738* (2013.01); *A61K 45/06* (2013.01); *C08B 37/006* (2013.01); *C08B 37/0045* (2013.01)

(58) Field of Classification Search
CPC .... A61K 31/715; A61K 31/738; A61K 45/06; C08B 37/006; C08B 37/0045
USPC .............................. 536/123, 2, 123.1; 514/54
See application file for complete search history.

(56) References Cited

U.S. PATENT DOCUMENTS

| 2,132,577 A | 10/1938 | Olsen et al. |
| 2,444,266 A | 6/1948 | Maclay et al. |
| 2,503,258 A | 4/1950 | Graham et al. |
| 4,016,351 A | 4/1977 | Eschinasi et al. |
| 4,268,533 A | 5/1981 | Williams et al. |
| 4,686,106 A | 8/1987 | Ehrlich et al. |
| 5,071,970 A | 12/1991 | Le Grand et al. |
| 5,498,702 A | 3/1996 | Mitchell et al. |
| 5,681,923 A | 10/1997 | Platt |
| 5,834,442 A | 11/1998 | Raz et al. |
| 5,895,784 A | 4/1999 | Raz et al. |
| 6,417,173 B1 | 7/2002 | Roufa et al. |
| 6,423,314 B2 | 7/2002 | Platt et al. |
| 6,500,807 B1 | 12/2002 | Platt et al. |
| 6,632,797 B2 | 10/2003 | Siren |
| 6,680,306 B2 | 1/2004 | Chang et al. |
| 6,756,362 B2 | 6/2004 | Roufa et al. |
| 6,770,622 B2 | 8/2004 | Jarvis et al. |
| 6,890,906 B2 | 5/2005 | Chang et al. |
| 7,491,708 B1 | 2/2009 | Platt et al. |
| 7,893,252 B2 | 2/2011 | Platt et al. |
| 8,128,966 B2 | 3/2012 | Staples et al. |
| 8,187,642 B1 | 5/2012 | Staples et al. |
| 8,236,780 B2 | 8/2012 | Platt et al. |
| 8,409,635 B2 | 4/2013 | Staples et al. |
| 8,420,133 B2 | 4/2013 | Staples et al. |
| 8,658,787 B2 | 2/2014 | Traber et al. |
| 8,828,971 B2 | 9/2014 | Traber et al. |
| 8,871,925 B2 | 10/2014 | Zomer et al. |
| 8,962,824 B2 | 2/2015 | Zomer et al. |
| 9,339,515 B2 | 5/2016 | Traber |

(Continued)

FOREIGN PATENT DOCUMENTS

| JP | H07-109226 | 4/1995 |
| JP | 2001-519471 | 10/2001 |
| JP | 2005-531576 | 10/2005 |
| WO | 85/05031 | 11/1985 |
| WO | WO 85/05031 | * 11/1985 |

(Continued)

OTHER PUBLICATIONS

Trisha Gura; Science, vol. 278, Nov. 7, 1997, 1041-1042.*
Ali et al. "Nitric Oxide Aguments Mesenchymal Stem Cell Ability to Repair Liver Fibrosis", Journal of Translation Medicine 2012, 10:75.

(Continued)

*Primary Examiner* — Shaojia Anna Jiang
*Assistant Examiner* — Michael C Henry
(74) *Attorney, Agent, or Firm* — Greenberg Traurig, LLP; Natalie Salem; Barry Schindler

(57) ABSTRACT

Aspects of the invention provide compositions for use in the treatment galectin-dependent diseases. In particular, compositions comprising a selectively depolymerized, branched galectoarabino-rhamnogalacturonate whose backbone is predominantly comprised of 1,4-linked galacturonic acid (GalA) moieties, with a lesser backbone composition of alternating 1,4-linked GalA and 1,2-linked rhamnose (Rha), which in-turn is linked to any number of side chains, including predominantly 1,4-b-D-galactose (Gal) and 1,5-α-L-arabinose (Ara) residues.

13 Claims, 27 Drawing Sheets

(17 of 27 Drawing Sheet(s) Filed in Color)

(56) References Cited

U.S. PATENT DOCUMENTS

| | | | |
|---|---|---|---|
| 9,646,327 | B2 | 5/2017 | Zomer et al. |
| 2003/0004132 | A1 | 1/2003 | Chang et al. |
| 2003/0013682 | A1 | 1/2003 | Banito et al. |
| 2004/0023925 | A1 | 2/2004 | Chang et al. |
| 2004/0043962 | A1 | 3/2004 | Chang et al. |
| 2004/0121981 | A1 | 6/2004 | Chang et al. |
| 2004/0223971 | A1 | 11/2004 | Chang et al. |
| 2005/0008572 | A1 | 1/2005 | Prokop et al. |
| 2005/0250735 | A1 | 11/2005 | Staples et al. |
| 2006/0094688 | A1* | 5/2006 | Tanaka .................. A61K 8/73 514/54 |
| 2006/0211653 | A1 | 9/2006 | Ni et al. |
| 2008/0089959 | A1 | 4/2008 | Chang et al. |
| 2008/0107622 | A1* | 5/2008 | Platt .................. A61K 31/715 424/85.2 |
| 2009/0217401 | A1 | 8/2009 | Korman et al. |
| 2011/0046086 | A1 | 2/2011 | Yun et al. |
| 2013/0261078 | A1 | 10/2013 | Zomer et al. |
| 2014/0086932 | A1 | 3/2014 | Traber |
| 2014/0350238 | A1 | 11/2014 | Zomer et al. |
| 2015/0147338 | A1 | 5/2015 | Traber et al. |

FOREIGN PATENT DOCUMENTS

| | | |
|---|---|---|
| WO | 99/19365 | 5/1999 |
| WO | 03/099308 | 12/2003 |
| WO | 2004/091634 | 10/2004 |
| WO | 2005/095463 | 10/2005 |
| WO | 2013/040324 | 3/2013 |
| WO | 2013/101314 | 7/2013 |
| WO | 2013/184892 | 12/2013 |
| WO | 2014/043708 | 3/2014 |

OTHER PUBLICATIONS

Banh et al. "Tumor Galectin-1 mediates tumor growth and metastasis through regulation of T-cell apoptosis", Cancer Res. 71:4423-31 (2011).

Barondes et al., "Galectins: a family of animal beta-galactoside-binding lectins [letter]", Cell. (76): 597-598 (1994).

Barrow et al., "The role of galectins in colorectal cancer progression," Int. J. Cancer. 129:1-8 (2011b).

Cay et al., "Review Immunohistochemical expression of galectin-3 in cancer: a review of the literature," Patoloji Derg. 28(1): 1-10 (2012).

De Smedt et al., "Effect of interieukin-IO on dendritic cell maturation and function", Eur J Immunol 27: 1229-1235, 1997.

Demotte et al., "A Galectin-3 Ligand Corrects the Impaired Function of Human CD4 and CD8 Tumor-Infiltrating Lymphocytes and Favor Tumor Refection in Mice", Cancer Res; 70(19) Oct. 1, 2010, pp. 7476-7488.

Demotte et al., "Restoring the Association of the T Cell Receptor with CD8 Reverses Anergy in Human Tumor-Infilitrating Lymphocytes", Immunity 28, pp. 414-424 Mar. 2008.

Driessens et al, Costimulatory and coinhibitory receptors in anti-tumor immunity. Immunol Rev 229:126-144, 2009.

Forsman et al., "Galectin 3 aggravates joint inflammation and destruction in antigen-induced arthritis", Arthritis Reum. 63: 445-454 (2011).

Fracanzani et al. "Contrast-Enhanced Doppler Ultrasonography in the Diagnosis of Hepatocellular Carcinoma and Premalignant Lesions in Patients with Cirrhosis", Hepatology 34: 1109-1112, 2001.

Godwin Avwioro, "Histochemical uses of Haematoxylln—A Review", JPCS. 1: 24-34 (2011).

Gura, "Systems for Identifying New Drugs are Often Faulty", Science, vol. 278, Nov. 7, 1997, 1041-1042

Kolatsi-Joannou et al., "Modified citrus pectin reduces galectin-3 expression and disease severity in experimental acute kidney injury", PLoS One. 6: 218683, doi: 10.1371/journal.pone.0018683 (2011).

Lefranc et al., "Galectin-1 mediated biochemical controls of melanoma and glioma aggressive behavior", World J. Biol. Chem. 2: 193-201 (2011).

Liu et al., "Galectins in regulation of inflammation and immunity", In Galectins (ed. by Klyosov, A.A., Witzhak, Z.A., and Platt, D.), John Wiley & Songs, Hoboken, New Jersey, pp. 97-113 (2008).

Lopez et al., "Gene expression profiling in lungs of chronic asthmatic mice treated with galectin-3: downregulation of inflammatory and regulatory genes", Mediators inglammm., 823279. Epub Mar. 20, 2011 (2011).

Newlaczyl et al., "Galectin-3—a jack-of-all-trades in cancer", Cancer Lett. 313: 123-128 (2011).

Office Action from Chinese Patent Application No. 201280068334.1 dated Jan. 4, 2016.

Office Action from Chinese Patent Application No. 201280068334.1 dated Jun. 15, 2015.

Office Action from U.S. Appl. No. 14/575,062 dated Apr. 22, 2016.

Office Action from U.S. Appl. No. 14/575,062 dated Dec. 18, 2014.

Office Action from U.S. Appl. No. 14/575,062 dated Feb. 2, 2015.

Office Action from U.S. Appl. No. 14/575,062 dated Oct. 26, 2016.

Ohshima et al., "Galectin 3 and its binding protein in rheumatoid arthritis", Arthritis Rehum. 48: 2788-2795 (2003).

Patra et al., "Structural characterization of an immunoenhancing heteropolysaccharide isolated from hot water extract of the fresh leaves of Catharanthus rosea", Carbohydrate Polymers 81 (2010): pp. 584-591.

Patra et al., "Structure elucidation of an immunoenhancing pectic polysaccharide isolated from aqueous extract of pods of green bean (*Phaseolus vulgaris* L.)", Carbohydrate Polymers 87 (2012), pp. 2169-2175.

Sato et al., "Galectins as danger signals in host-pathogen and hot-tumor interactions: new members of the growing group of Alarmins." In Galectins, (Klyosov, et al eds.) John Wiley & Sons, 115-145 (2008).

Sun et al., "Structural Characterization of a Tobacco Rhamnogalacturonan", Carbohydrate Polymers 7 (1987) pp. 143-158.

Supplementary European Search Report from European Application No. 12831657.7 dated Mar. 20, 2015.

Supplementary European Search Report from European Application No. 12863426.8 dated Apr. 28, 2015.

Toussaint et al., "Galectin-I, a gene preferentially expressed at the tumor margin, promotes glioblastoma cell invasion", Mol Cancer. 11: 32 (2012).

Wang et al., "Nuclear and cytoplasmic localization of galectin-1 and galectin-3 and their roles in pre-mRNA splicing", In Galectins (Klyosov et al eds.), John Wiley & Songs, 87-95 (2008).

Yapo, "Rhamnoagalcturonan-1: A Structurally Puzzling and Functionally Versatile Polysaccharide from Plant Cell Walls and Mucilages", Polymer Reviews, 51:4, 391-413, Oct. 2011.

Zhan et al., "Scarcity or complete lack of single rhamnose residues interspersed within the homogalacturonan regions of citrus pectin", Carbohydrate Research 308 (1998), pp. 373-380.

Erdman et al., "CD4+CD25+ Regulatory Lymphocytes Induce Regression of Intestinal Tumors in ApcMin/+ Mice", Cancer Res 2005, 65(10): 3998-4004.

Lamichhane et al., "PD-1 and IL-10: partners in crime against anti-tumor immunity in ovarian cancer", Ther Journal of Immunology, May 1, 2015, vol. 194, No. 1.

Park et al., "Diverse Roles of Invariant Natural Killer T Cells in Liver Injury and Fibrosis Induced by Carbon Tetrachloride", Hepatology, May 2009, 49(5), pp. 1683-1694.

\* cited by examiner

| Study Number | Sample ID | Results (Daltons) |
|---|---|---|
| 3098-003 | Compound G | 36,950 [STD 8%] |

Results:

| Sample ID | RT | Area | % area | MW Range (Daltons) |
|---|---|---|---|---|
| 4828-06-09 | 8.056 | 8906130 | 100% | 20 K – 70 K |

Thioacetamide-Induced Fibrosis in Rats

TAA 150mg/kg 3x/wk(11 weeks)

4 weeks Rx   All given intra-peritoneally 0.9% NaCl (similar volume 2X/week)

Compound G (90 mg/kg 1X/week)

Compound D (180 mg/kg 1X/week)

COMPOSITION OF NOVEL CARBOHYDRATE DRUG FOR TREATMENT OF HUMAN DISEASES

RELATED APPLICATIONS

This application is a continuation of U.S. application Ser. No. 14/575,062, filed Dec. 18, 2014, which is a continuation of U.S. application Ser. No. 14/456,644, filed Aug. 11, 2014, now U.S. Pat. No. 8,962,824, which is a continuation of U.S. application Ser. No. 13/573,442, filed Sep. 14, 2012, now U.S. Pat. No. 8,871,925, which claims the benefit of and priority to U.S. provisional Application Ser. No. 61/580,830, filed Dec. 28, 2011, the entire disclosures of each of which are incorporated herein by reference in their entireties.

FIELD OF THE INVENTION

Aspects of the invention relate to a pharmaceutical-grade polysaccharide, pharmaceutical compositions thereof and to methods of manufacturing the same. Other aspects of the invention relate to methods of treating disease conditions, such as medical conditions related to inflammation and fibrosis and cancer linked at least in part to aberrant or increased expression of galectin proteins, using these compounds and compositions.

BACKGROUND OF THE INVENTION

Plants and plant products have been used for many years to derive pharmaceutical products, often in the form of specific complex organic molecules that have physiological function in animals and human. In addition to single specific molecules, the structural components of the plant cell, which are large, complex carbohydrate molecules, have been explored for various effects on animals and humans in normal physiology and disease. Among the complex carbohydrates that make up the cell walls of plant cells, pectins represent a class of molecules that have been extensively examined.

In order to evaluate the effect of pectins in the systemic circulation and organs of animals and humans, attempts have been made to develop modified pectins that could be utilized as medicinal compounds.

Accordingly, there is a need to provide modified pectins and method of manufacturing modified pectins for use as parenteral or enteral medicinal compounds. Moreover, there is a need to for these compounds to have the required pharmacological properties to inhibit inflammation and fibrosis while remaining non-toxic to other cells and tissues.

SUMMARY OF THE INVENTION

Aspects of the invention relate to a compound or composition comprising a compound in an acceptable pharmaceutical carrier for parenteral or enteral administration, for use in therapeutic formulations.

In some embodiments, the compound is a polysaccharide and may be chemically defined as arabinogalacto-rhamnogalacturonan (herein referred to as Compound G), a selectively depolymerized, branched heteropolymer whose backbone is predominantly comprised of 1,4-linked galacturonic acid (GalA) and methyl galacturonate (MeGalA) residues, with a lesser backbone composition of alternating 1,4-linked GalA and 1,2-linked rhamnose (Rha), which in-turn is linked to any number of oligomer side chains, including predominantly 1,4-β-D-galactose (Gal), 1,5-α-L-arabinose (Ara) residues or combination thereof. Other side chain minor constituents may include xylose (Xyl), glucose (Glu), fucose (Fuc) or any combination of the foregoing.

In some embodiments, the arabinogalacto-rhamnogalacturonan compound of the present invention (Compound G) is capable of reducing the secretion of TNF-alpha cytokine from monocytes stressed with endotoxin. In some embodiments, the compound G is capable of reducing the secretion of TNF alpha by activated macrophages by at least 25%.

In some embodiments, the 1,4-linked galacturonic acid and methyl galacturonate residues backbone can represent between 55 to 85 molar percent of the total carbohydrate molar content, the branched heteropolymer of alternating α-1,2 linked rhamnose and α-1,4-linked GalA residues can represent between 1 and 6 molar percent of the total carbohydrate molar content, the oligomer 1,4-β-D-galactose of the primary branching can represent between 6 to 15 molar percent of the total carbohydrate molar content and the oligomer 1,5-α-L-arabinose of the primary branching can represent between 2 to 8 molar percent of the total carbohydrate molar content, as characterized by gas chromatography/mass spectrometry.

In some embodiments, the oligomer of 1,4-β-D-galactose residues, 1,5-α-L-arabinose residues or combinations thereof represents at least 8 molar percent of the total carbohydrate molar content.

In some embodiments, the 1,4-β-D-galactose and 1,5-α-L-arabinose residues are present in a 2:1 to a 3:1 ratio in the arabinogalacto-rhamnogalacturonan compound of the present invention.

In some embodiments, the compound of the present invention has a degree of methoxylation ranging from 40% to 70% of the maximum of 87%.

In some embodiments, the compound of the present invention has a methyl galacturonate to galacturonic acid ratio ranging from 2:1 to 1:2.

In some embodiments, the compound of the present invention has a methyl galacturonate plus galacturonic acid ratio to galactose ranging from 4:1 to 7:1.

In some embodiments, the molar percent of the 1,4-β-D-Gal and 1,5-α-L-Ara residues in the compound of the present invention can exceed 10% of the total molar carbohydrates with approximate ratio ranging from 1:1 to 3:1 respectively.

In some embodiments, the compound is a polysaccharide chemically defined as galactoarabino-rhamnogalacturonate (Compound G), a branched heteropolymer with average molecular weight distribution of 2,000 to 80,000, or 20,000 to 70,000, or 5,000 to 55,000 Daltons, as determined by SEC-RI and/or the SEC-MALLS method.

In some embodiments, the compound can be a highly soluble modified polysaccharide sufficiently reduced in average molecular weight, for example from about 2,000 to about 80,000 D, so as to be compatible with therapeutic formulations for pluralistic administration via routes including but not limited to intravenous, subcutaneous, intra-articular, inhaled, and oral.

In some embodiments, the compound can be substantially free of microbial endotoxin, agricultural pesticides, agricultural herbicides, copper, heavy metals, proteins, nitrogenous compounds or any combination of the foregoing.

In some embodiments, the compound can be synthesized from natural, highly branched, minimally processed and high methoxylated USP pectin which may come from any plant source, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments the compound can be produced by a process comprising depolymerization catabolized by targeted peroxidation cleavage of glycosidic bonds by ionized OH sup-generated from ascorbic acid and/or peroxide in presence or absence of additional reduced form of a transition metal ion, like Cu sup.++ at 1 to 100 mM. Other transition metals like Ca. sup.++ or Fe.sup.++ can also be used for this purpose.

In some embodiments, the depolymerized compound can be exposed to pH of between 8 to 10 for 10 to 30 minutes at temperature of 2 to 60° C. to initiate controlled limited demethoxylation to generate a depolymerized compound with a degree of methoxylation of 40 to 70 percent in comparison to initial levels of maximum 87% and can be referred to as middle-methoxylated compound. Complete methoxylation of galacturonic acid is considered to be approximately DE 87%.

In some embodiments, the depolymerized composition can be exposed to multiple washes of hot acidic alcohol (e.g at temperatures ranging from 30 to 80° C.) to remove any residual endotoxin, copper and heavy metals, agricultural contaminates and other impurities.

In some embodiments, the compound does not induce decreased viability when used to treat LX2 immortalized human hepatic stellate cells.

In some embodiments, the compound is capable of reducing expression of galectin-3 at the cell surface or substantial decrease in secretion of galectin-3 in the media when used to treat stressed LX2 immortalized human hepatic stellate cells producing galectin-3.

Aspects of the invention relate to an arabinogalactorhamnogalcturonan compound comprising a 1,4-linked galacturonic acid (GalA) and methyl galacturonate (MeGalA) residues backbone linked to branched heteropolymers of alternating oligomers of α-1,2 linked rhamnose and α-1,4-linked GalA residues, the rhamnose residues carrying a primary branching of oligomers of 1,4-β-D-galactose residues, 1,5-α-L-arabinose residues, or combinations thereof, wherein the compound is capable of reducing the secretion of TNF alpha cytokine from monocytes stressed with endotoxin, wherein the compound does not inhibit cancer cell proliferation in a cancer cell apoptosis or a cytotoxic model, and wherein the compound is not cytotoxic to monocytes or activated monocytes.

In some embodiments, the compound does not inhibit cancer cell proliferation in a cancer cell and is not cytotoxic to monocytes or activated monocytes at concentrations up to 500 µg/mL.

In some embodiments, the 1,4-linked galacturonic acid and the methyl galacturonate residues backbone can represent between 55 to 85 molar percent of the total carbohydrate molar content, the branched heteropolymer of alternating α-1,2 linked rhamnose and α-1,4-linked GalA residues can represent between 1 and 3 molar percent of the total carbohydrate molar content, the oligomer 1,4-β-D-galactose of the primary branching can represent between 6 to 15 molar percent of the total carbohydrate molar content and the oligomer 1,5-α-L-arabinose of the primary branching can represent between 2 to 8 molar percent of the total carbohydrate molar content, as characterized by gas chromatography/mass spectrometry.

In some embodiments, the 1,4-β-D-galactose residues, 1,5-α-L-arabinose residues or combination thereof can represent at least 8 molar percent of the total carbohydrate molar content.

In some embodiments, the 1,4-β-D-galactose and 1,5-α-L-arabinose residues can be present in a 2:1 ratio.

In some embodiments, the compound can have an average molecular weight ranging from 5 kDa to 55 kDa or ranging from 2 kDa to 70 kDa.

In some embodiments, the compound can have a degree of methoxylation ranging from 40% to 70% out of maximum 87%.

In some embodiments, the compound can have a methyl galacturonate to galacturonic acid ratio ranging from 2:1 to 1:2.

In some embodiments, the compound can have a methyl galacturonate plus galacturonic acid ratio to galactose ranging from 4:1 to 8:1.

In some embodiments, the compound does not induce decreased viability when used to treat LX2 immortalized human hepatic stellate cells.

In some embodiments, the compound is capable of inducing substantial decrease in expression of galectin-3 at the cell surface or substantial decrease in secretion of galectin-3 in the media when used to treat stressed LX2 immortalized human hepatic stellate cells producing galectin-3.

Aspects of the invention relate to compositions comprising a compound in an acceptable pharmaceutical carrier for use in therapeutic formulations. In some embodiments, the composition can be administered parenterally via an intravenous, subcutaneous, or oral route.

In some embodiments, the composition can further comprise a therapeutic agent. For example, the therapeutic agent can be an anti-oxidant compound, an anti-inflammatory agent, vitamins, a neutraceutical supplement or combinations thereof.

In some embodiments, the composition can be used in the treatment of nonalcoholic steatohepatitis, fibrosis, inflammatory and autoimmune disorders, neoplastic conditions or of cancer.

In some embodiments, the composition can be used in the treatment of liver fibrosis, kidney fibrosis, lung fibrosis, or heart fibrosis.

In some embodiments, the invention relates to a composition or a compound utilized in treating or a method of treating inflammatory and fibrotic disorders in which galectins are at least in part involved in the pathogenesis, including but not limited to enhanced anti-fibrosis activity in organs, including but not limited to liver, kidney, lung, and heart.

In some embodiments, the invention relates to a composition or a compound that has therapeutic activity or a method to reduce the pathology and disease activity associated with nonalcoholic steatohepatitis (NASH) including but not limited to steatosis (fat accumulation in hepatocytes), ballooning degeneration of hepatocytes, inflammatory infiltrate in the liver, and deposition of collagen or fibrosis.

In some embodiments, the invention relates to a composition or a compound utilized in treating or a method of treating inflammatory and autoimmune disorders in which galectins are at least in part involved in the pathogenesis including but not limited to arthritis, rheumatoid arthritis, asthma, and inflammatory bowel disease.

In some embodiments, the invention relates to a composition or a compound utilized in treating or a method of treating neoplastic conditions (e.g. cancers) in which galectins are at least in part involved in the pathogenesis by inhibiting processes promoted by the increase in galectins, including but not limited to tumor cell invasion, metastasis, and neovascularization.

In some embodiments, the invention relates to a composition or a compound utilized in enhancing or a method for enhancing the ability of tumor infiltrating T-cells, which are inhibited at least in part by the effect of tumor derived galectin proteins, to more effectively identify and kill tumor cells and thereby slow, stop or reverse the progression of tumors.

In some embodiments, a therapeutically effective amount of the depolymerized compound or of the composition can be compatible and effective in combination with a therapeutically effective amount of various anti-inflammatory drugs, vitamins, other pharmaceuticals and nutraceuticals drugs, without limitation.

In some embodiments, a therapeutically effective amount of the depolymerized compound or of the composition can be compatible and effective in combination with a therapeutically effective amount of various anti-oxidant compounds such as glycyrrhizin, ascorbic acid, L-glutathione, cysteamine and the like or combinations thereof.

In some embodiments, a therapeutically effective amount of the compound or of the composition can be non-toxic and does not induce apoptosis in cultured cell lines when added to cell culture media including but not limited to the cell lines LX-2, or other stellate cells.

In some embodiments, a therapeutically effective amount of the compound or of the composition is not cytotoxic to mammalian cultured cells when added to cell culture media including but not limited to B16-F10 melanoma cells, THP-1 monocyte/macrophage cells, primary peripheral blood mononuclear cells (PBMC) and MRC-5 lung fibroblast cells.

In some embodiments, a therapeutically effective amount of the compound or of the composition can have an anti-inflammatory effect on cell lines as measured by production of pro-inflammatory cytokines including but not limited to TNF-alpha.

In some embodiments, efficacy of the compound or of the composition for treatment of liver fibrosis can be determined by administering the compound or composition to animal models of fibrosis including but not limited to rats injected intraperitoneally with the chemical toxin thioacetamide, resulting in at least 5% to 25% reduction in liver collagen content as determined by morphometric quantification.

In another embodiment, efficacy of the composition for treatment of NASH can be determined by administering the compound or composition to animal models of NASH including but not limited to mice rendered diabetic and fed a high fat diet, resulting in at least 5% reduction in hepatocellular fat accumulation, at least a 5% reduction in the number of hepatocytes with ballooning degeneration, at least 5% reduction in liver infiltration of inflammatory cells, and at least a 5% reduction in liver collagen content as determined by morphometric quantification (assessed by staining positive for Sirius red).

In another embodiment, administering a therapeutically effective amount of the depolymerized compound or of the composition to an animal model of NASH can result in reduction of fibrosis as measured by standard histopathology of biopsies, reduction in disease activity by NAFLD grading, a decrease in the number of cells expressing alpha Smooth Muscle Actin, or a decrease in other inflammatory mediators or a decrease in lipid trafficking and metabolism enzymes including but not limited to CD36.

In another embodiment, administering a therapeutically effective amount of the depolymerized compound or of the composition can result in reduction of galectin-3 as measured by either level of mRNA or the expression of the galactose binding protein.

In another embodiment, administering a therapeutically effective amount of the depolymerized compound or of the composition can result in reduced growth, invasion, metastasis, or increased sensitivity to the innate immune system of syngeneic or xenotopic tumors in animals.

These and other aspects of the present invention will become apparent upon reference to the following detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 6a is a graph showing the incorporation of radiolabeled thymidine in cultured LX-2 cells. FIG. 6b is a graph showing the evaluation of cellular viability in cultured LX-2 cells. FIG. 6c depicts an assessment of apoptosis and cell cycle by FACS in cultured LX-2 cells. FIG. 6d shows an assessment of apoptosis by DNA fragmentation in cultured LX-2 cells using Annexin V apoptosis detection kit APC (eBioscience).

FIG. 19A shows the NAFLD activity score in mice treated with vehicle, Compound D, and Compound G for 6 to 9 weeks (Early Rx). FIG. 19B shows the NAFLD activity score in mice treated with vehicle, Compound D, and Compound G for 9-12 weeks (Late Rx).

FIG. 20A shows the Sirius-Red positive area (%) in mice treated with vehicle, Compound D, and Compound G for 6 to 9 weeks (Early Rx). FIG. 20B shows the Sirius-Red positive area (%) in mice treated with vehicle, Compound D, and Compound G for 9-12 weeks (Late Rx).

DETAILED DESCRIPTION OF THE INVENTION

Figure 1:
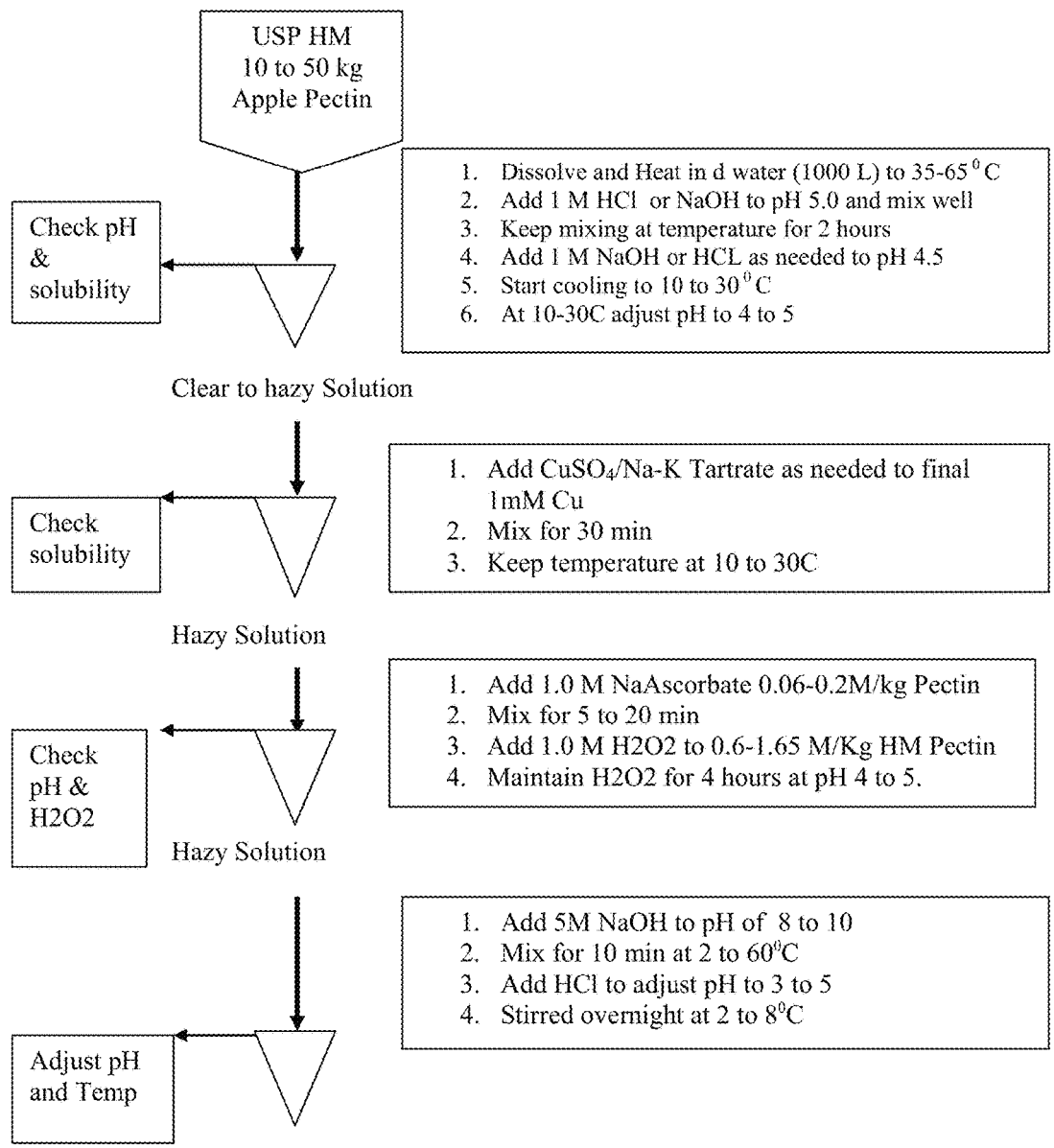
FIG. 1 shows a schematic of a manufacturing process flow chart that may be utilized in one embodiment to manufacture Compound G, the active pharmaceutical ingredient.
Figure 1:
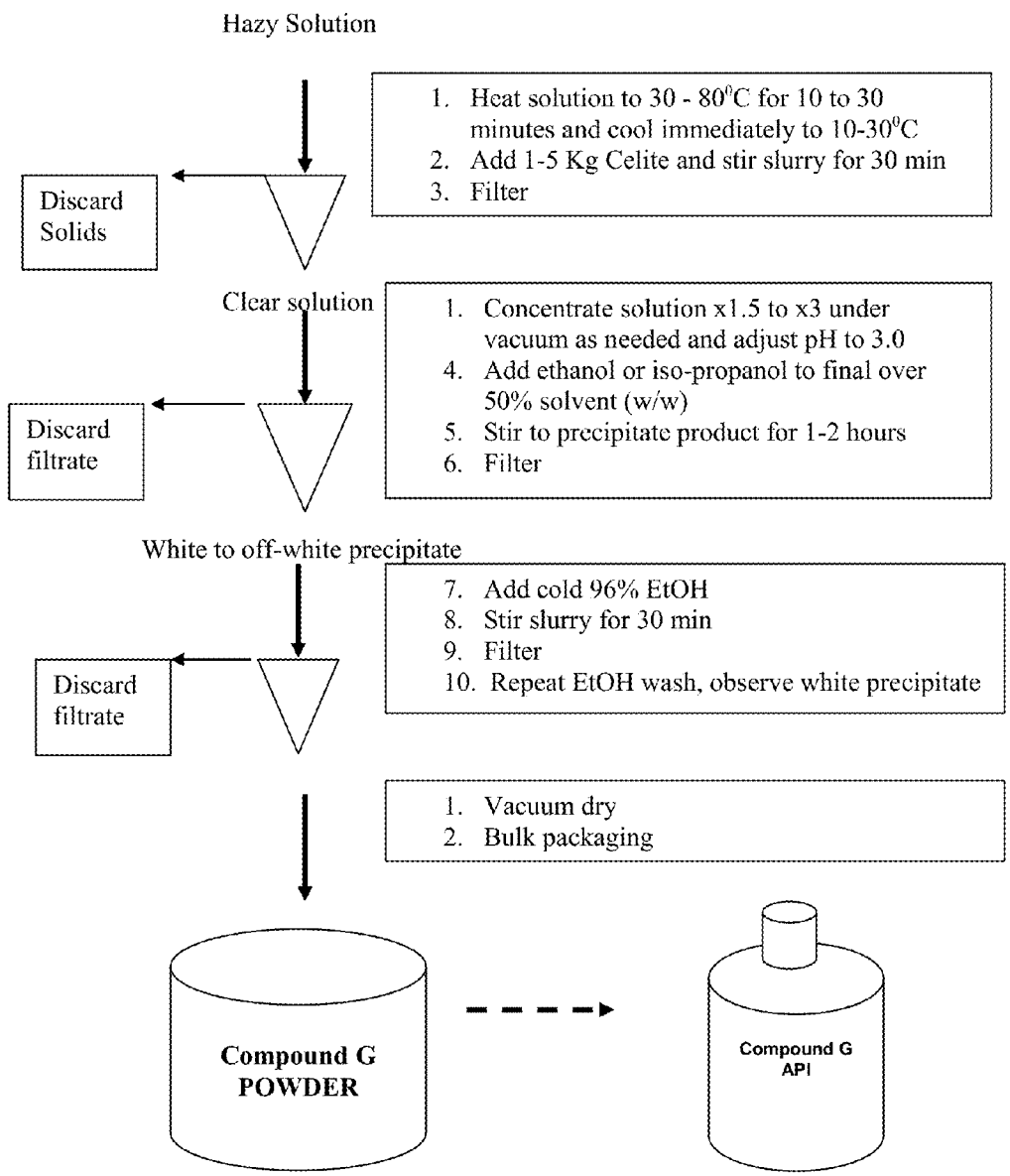

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Citation of documents herein is not intended as an admission that any of the documents cited herein is pertinent prior art, or an admission that the cited documents are considered material to the patentability of the claims of the present application.

Unless otherwise specified, all percentages expressed herein are weight/weight.

Pectins are comprised of diversified large carbohydrate polymers that are composed of a backbone of polymeric galacturonic acid with periodic interspersed rhamnose molecules and periodic branched chains of various carbohydrates including galactose, arabinose, fucose, glucose, and others. The galacturonic acid molecules are naturally modified by methoxylation at a high percentage of the residues.

The large pectin carbohydrate polymers have been studied in their native form (directly after extraction from plants) and after various degrees of modification which hydrolyze and chemically modify the polymers. While modified pectins are widely used in the food industry for their ability to gel and provide consistency to various food preparations, they have also been evaluated as potential medicinal compounds.

Plant-derived pectin materials, both unaltered and modified, have been extensively evaluated when administered orally to animals and humans. A variety of effects of orally administered unaltered and modified pectins have been described including increased satiety, weight loss, modification of bowel motility, and effects on bowel function including salutatory effects on constipation and diarrhea. Ingested pectin material is not digested by normal gut enzymes nor absorbed by the intestine. Therefore, there is little to no pectin that is absorbed into the blood stream after oral absorption.

In order to evaluate the effect of pectins and modified pectin molecules in the systemic circulation and organs of animals and humans, attempts have been made to develop modified pectins that could be utilized as parenteral compounds. Pectin derived from a mixture of citrus fruit has been evaluated in cell culture models and in animal models of disease, particular in cancer cells and models of cancer in animals. The use of modified citrus pectin has been shown to cause cytotoxicity and apoptosis in animal cell lines. Such modified citrus pectin has been proposed to be useful in malignant conditions (See U.S. Pat. No. 8,128,966).

Galectins

Galectins (also known as galaptins or S-lectin) are a family of lectins which bind beta-galactoside. Galectin as general name was proposed in 1994 for a family of animal lectins (Barondes, S. H., et al.: Galectins: a family of animal beta-galactoside-binding lectins. Cell 76, 597-598, 1994), The family is defined by having at least one characteristic carbohydrate recognition domain (CRD) with an affinity for beta-galactosides and sharing certain sequence elements. Within the same peptide chain, some galectins have a CRD with only a few additional amino acids, whereas others have two CRDs joined by a link peptide, and one (galectin-3) has one CRD joined to a different type of domain. The galectin carbohydrate recognition domain (CRD) is a beta-sandwich of about 135 amino acids. The two sheets are slightly bent with 6 strands forming the concave side and 5 strands forming the convex side. The concave side forms a groove in which carbohydrate is bound (Leffler H, Carlsson S, Hedlund M, Qian Y, Poirier F (2004). "Introduction to galectins". Glycoconj. J. 19 (7-9): 433-40).

A wide variety of biological phenomena have been shown to be related to galectins, e.g., development, differentiation, morphogenesis, tumor metastasis, apoptosis, RNA splicing, etc. However, relatively little is known about the mechanism by which galectins exert these functions, particularly in terms of carbohydrate recognition.

Generally, the carbohydrate domain binds to galactose residues associated with glycoproteins. At least fifteen mammalian galectin proteins have been identified which have one or two carbohydrate domain in tandem.

Galectin proteins are found in the intracellular space where they have been assigned a number of functions and are secreted into the extracellular space. In the extracellular space, galectin proteins can have multiple functions including promoting interactions between glycoproteins that may lead to reduced function, or enhanced functions, or in the case of integral membrane glycoprotein receptors, modification of cellular signaling (Sato et al "Galectins as danger signals in host-pathogen and host-tumor interactions: new members of the growing group of "Alarmins." In "Galectins," (Klyosov, et al eds.), John Wiley and Sons, 115-145, 2008, Liu et al "Galectins in acute and chronic inflammation," Ann. N. Y. Acad. Sci. 1253: 80-91, 2012). Galectin proteins in the extracellular space can additionally promote cell-cell and cell matrix interactions (Wang et al., "Nuclear and cytoplasmic localization of galectin-1 and galectin-3 and their roles in pre-mRNA splicing." In "Galectins" (Klyosov et al eds.), John Wiley and Sons, 87-95, 2008).

Galectins have been shown to have domains which promote homodimerization. Thus, galectins are capable of acting as a "molecular glue" of sorts between glycoproteins. Galectins are found in multiple cellular compartments, including the nucleus and cytoplasm, and are secreted into the extracellular space where they interact with cell surface and extracellular matrix glycoproteins. The mechanism of molecular interactions can depend on the localization. While galectins can interact with glycoproteins in the extracellular space, the interactions of galectin with other proteins in the intracellular space generally occurs via protein domains. In the extracellular space the association of cell surface receptors may increase or decrease receptor signaling or the ability to interact with ligands. Galectin proteins are markedly increased in a number of animal and human disease states, including but not limited to diseases associated with inflammation, fibrosis, autoimmunity, and neoplasia. Galectins have been directly implicated in the disease pathogenesis, as described below. For example, diseases states that may be dependent on galectins include, but are not limited to, acute and chronic inflammation, allergic disorders, asthma, dermatitis, autoimmune disease, inflammatory and degenerative arthritis, immune-mediated neurological disease, fibrosis of multiple organs (including but not limited to liver, lung, kidney, pancreas, and heart), inflammatory bowel disease, atherosclerosis, heart failure, ocular inflammatory disease, a large variety of cancers.

In addition to disease states, galectins are important regulatory molecules in modulating the response of immune cells to vaccination, exogenous pathogens and cancer cells.

One of skill in the art will appreciate that compounds that can bind to galectins and/or alter galectin's affinity for glycoproteins, reduce hetero- or homo-typic interactions between galectins, or otherwise alter the function, synthesis, or metabolism of galectin proteins may have important therapeutic effects in galectin-dependent diseases.

Galectins show an affinity for galactose residues attached to other organic compounds, such as in lactose [(β-D-Galactosido)-D-glucose], N-acetyllactosamine, poly-N-acetyllactosamine, galactomannans, fragments of pectins, as well as other galactose containing compounds. It should be noted that galactose by itself does not bind to galectins, or binds so weakly that the binding can hardly be detected.

Pectin and modified pectin have been shown to bind to galectin proteins presumably on the basis of containing galactose residues that are presented in the context of a macromolecule, in this case a complex carbohydrate rather than a glycoprotein in the case of animal cells.

Galectin proteins have been shown to be markedly increased in inflammation, fibrotic disorders, and neoplasia (Ito et al. "Galectin-1 as a potent target for cancer therapy: role in the tumor microenvironment", Cancer Metastasis Rev. PMID: 22706847 (2012), Nangia-Makker et al. Galectin-3 binding and metastasis," Methods Mol Biol. 878: 251-266, 2012, Canesin et al. Galectin-3 expression is associated with bladder cancer progression and clinical outcome," Tumour Biol. 31: 277-285, 2010, Wanninger et al. "Systemic and hepatic vein galectin-3 are increased in patients with alcoholic liver cirrhosis and negatively correlate with liver function," Cytokine. 55: 435-40, 2011. Moreover, experiments have shown that galectins, particularly galectin-1 and galectin-3, are directly involved in the pathogenesis of these classes of disease (Toussaint et al., "Galectin-1, a gene preferentially expressed at the tumor margin, promotes glioblastoma cell invasion.", Mol Cancer. 11:32, 2012, Liu et al 2012, Newlaczyl et al., "Galectin-3—a jack-of-all-trades in cancer," Cancer Lett. 313: 123-128, 2011, Banh et al., "Tumor galectin-1 mediates tumor growth and metastasis through regulation of T-cell apoptosis," Cancer Res. 71: 4423-31, 2011, Lefranc et al., "Galectin-1 mediated biochemical controls of melanoma and glioma aggressive behavior," World J. Biol. Chem. 2: 193-201, 2011, Forsman et al., "Galectin 3 aggravates joint inflammation and destruction in antigen-induced arthritis," Arthritis Reum. 63: 445-454, 2011, de Boer et al., "Galectin-3 in cardiac remodeling and heart failure," Curr. Heart Fail. Rep. 7, 1-8, 2010, Ueland et al., "Galectin-3 in heart failure: high levels are associated with all-cause mortality," Int J Cardiol. 150: 361-364, 2011, Ohshima et al., "Galectin 3 and its binding protein in rheumatoid arthritis," Arthritis Rheum. 48: 2788-2795, 2003).

Therefore, there is a need to identify therapeutics that have affect galectins involved in human disorders, such as inflammatory diseases, fibrotic diseases, neoplastic diseases or combinations thereof, and that have a reliable safety profile, so as to be used in therapeutics.

Chemically Modified Pectins and Compositions

Compositions comprising a chemically modified pectin derived from apple pectin and methods of manufacturing such modified apple pectin having an activity in a cellular assay of inflammatory fibrosis have been previously described [see U.S. Pat. No. 8,236,780, incorporated herein by reference in its entirety]. Such modified pectin has been shown to reduce the induction of liver derived fibrogenic cells while having no effect on viability of the cells.

Aspects of the invention relate to a chemically modified pectin or modified pectin composition and methods of producing a modified pectin or modified pectin composition having an anti-inflammatory and/or anti-fibrogenic effects. In some embodiments, the modified pectin is a polysaccharide chemically defined as galactoarabino-rhamnogalacturonate.

Compositions for parenteral or enteral administration to a subject are disclosed herein. In some embodiments, the composition can comprise a pectin derivative or modified pectin compound of the invention in an acceptable pharmaceutical carrier. The term "pharmaceutically acceptable carrier" refers to a carrier or adjuvant that may be administered to a subject (e.g., a patient), together with a compound of this invention, and which does not destroy the pharmacological activity thereof and is nontoxic when administered in doses sufficient to deliver a therapeutic amount or an effective mount of the compound.

"Pharmaceutically acceptable carrier" refers to any and all solvents, dispersion media, e.g., human albumin or cross-linked gelatin polypeptides, coatings, antibacterial and antifungal compounds, isotonic, e.g., sodium chloride or sodium glutamate, and absorption delaying compounds, and the like that are physiologically compatible. The use of such media and compounds for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

In some embodiments, the modified pectin compound is obtained from a pharmaceutical-grade pectin.

In some embodiments, the modified pectin of the present invention can have an enhanced anti-inflammatory and/or an enhanced anti-fibrogenic effects when compared to previous pectin compositions. In various embodiments, the modified pectin of the present invention can inhibit secretion of Tumor necrosis factor (TNF-α, cachexin), a protein involved in systemic inflammation and a major member of a group of cytokines that stimulate the acute phase reaction. It is produced chiefly by activated macrophages. In various embodiments, the modified pectin of the present invention does not cause cytotoxicity. In various embodiments, the modified pectin or modified pectin composition has potent anti-inflammatory and anti-fibrosis properties without exhibiting cytotoxicity. This represents a novel and unexpected combination of effects which suggest that the pharmaceutical-grade modified pectin can have important effects in the treatment of human inflammatory diseases, fibrotic diseases, neoplastic diseases or combinations thereof.

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions in which galectins are involved, in a subject in need thereof are featured. The methods include administering to the subject an effective amount of a compound of the invention, or a composition comprising the compound of the invention, to the subject.

As used herein, the term "effective dose" refers to the amount of a compound that, alone or in combination with an amount of a therapeutic agent, when administered as a parental, subcutaneous, inhaled, intra-articular, ocular, or oral formulation or to an animal or human with a galectin-dependent inflammatory, fibrotic or neoplastic disease results in reduction in disease activity, as defined below in various embodiments.

"Administration" refers to oral, or parenteral including intravenous, subcutaneous, topical, transdermal, intradermal, transmucosal, intraperitoneal, intramuscular, intracapsular, intraorbital, intracardiac, intratracheal, subcutaneous, subcuticular, intraarticular, subcapsular, subarachnoid, intraspinal, epidural and intrasternal injection and infusion.

In some embodiments, the galactoarabino-rhamnogalacturonate compound has terminal galactose residues that can constitute the main binding entity to galectin proteins. The remaining side chain composition may stabilize or enhance its interaction with galectin proteins and thereby potentiate the compound's therapeutic action. Interaction with galectins may not be the only mechanism by which Compound G exerts its therapeutic action. While not wishing to be bound by speculation, the branched galactoarabino-rhamnogalacturonate compound of the invention can interact with galectin proteins and can have wide therapeutic effects that have not been seen with galactose or small molecules derivatives of galactose.

In some embodiments, the compound of the instant invention is a polysaccharide chemically defined as galactoarabino-rhamnogalacturonate (also referred herein as "Compound G"), a branched heteropolymer having a backbone characterized as a majority homopoly 1,4-linked galacturonic acid (GalA) molecules and methyl galacturonate (MeGalA) residues with intermittent short regions of alternating α-1,4-linked GalA and α-1,2-linked rhamnose (Rha), whereas the Rha units are further linked to side-chains. These side chains consist predominantly of 1,4-β-D-galactose residues (Gal) and/or 1,5-α-L-arabinose residues (Ara). Other carbohydrates may be present in small amount on the Gal and Ara side chains such as L-xylose (Xyl), D-glucose (Glu) and L-fucose (Fuc) residues. As used herein, the term "backbone" refers to the major chain of a polysaccharide, or the chain originating from the major chain of a starting polysaccharide, having saccharide moieties sequentially linked by either alpha or beta glycosidic bonds. A backbone may comprise additional monosaccharide moieties connected thereto at various positions along the sequential chain.

In some embodiments, Compound G is a chemically controlled modified natural branched heteropolymer of plant polysaccharides, some of which are available commercially as USP pectin material. These natural pectin materials are of high average molecular weight ranging from 40,000 to over 1,000,000 Daltons (D) and are crude mixtures. Most common USP pectins are from citrus fruit, apple and beets, although others are also available.

In some embodiments, the Compound G composition can have a an average molecular weight range of 2,000 to 80,000 D. In some embodiments, the average molecular weight of the compound G can range from 20,000 to 70,000 D. In specific examples, the galactoarabino-rhamnogalacturonate may have an average molecular weight of 5,000 to 55,000 D. Such galactoarabino-rhamnogalacturonate compounds can be obtained preferably through chemical and physical treatments and purification from natural pectic substance of apple pectin. However compounds similar to Compound G may be obtained from citrus, sugar beet pectin and other plants under appropriate extraction and chemical processing.

In one embodiment, the selectively depolymerized galactoarabino-rhamnogalacturonate (Compound G), a branched heteropolymer, can have an average molecular weight of 2,000 to 80,000, or 20,000 to 70,000, or 5,000 to 55,000 Daltons, as determined by SEC-RI and MALLS method. As used herein, the term "depolymerization" refers to partial, selective or complete hydrolysis of the polysaccharide backbone occurring, for example, when the polysaccharide is treated chemically resulting in fragments of reduced size when compared with the original polysaccharide.

Methods for Producing Compound G

Aspects of the invention relate to methods for producing selectively depolymerized galactoarabino-rhamnogalacturonate. In some embodiments, the process of the instant invention includes methods intended to preserve the structure and/or beta galactose characteristics and galactose binding abilities of the side chains comprised primarily of galactose and arabinose, and to enhance the prevalence of galactose binding moieties in the galactoarabino-rhamnogalacturonate compound. In some embodiments, the methods can generate a galactoarabino-rhamnogalacturonate compound having a reduced average molecular weight, so as to be compatible with therapeutic formulations for pluralistic administration via routes, including but not limited to, intravenous, subcutaneous, inhaled, intra-articular, ocular, and oral.

In some embodiments, the compound can be synthesized from natural, highly branched, minimally processed and high methoxylated USP pectin which may come from any plant source, including but not limited to, citrus fruits, apple, or beet.

In some embodiments, the compound can be synthesized from natural, highly branched, minimally processed and high methoxylated USP pectin like one manufactured from apple pomace containing 8-12% pectin.

In some embodiments, the compound can be synthesized under a sufficiently controlled and specific hydrolysis of the glycosidic-linked methoxylated α-1,4-linked GalA while preserving the side-chains with enriched amounts of 1,4-β-D-Gal and 1,5-α-L-Ara. Amounts of 1,4-β-D-Gal and 1,5-α-L-Ara can be quantitatively determined by GC-MS (Gas chromatography-mass spectroscopy) and AELC-PAD (anion exchange liquid chromatography-pulsed amperometric detector) methods.

In some embodiments, the compound can be produced by a process comprising depolymerization catabolized by targeted peroxidation cleavage of glycosidic bonds (also known as beta elimination reaction) by ionized OH supgenerated from ascorbic acid and/or peroxide in presence of a reduced form of a transition metal ion, like $Cu^{++}$ at 1 to 100 mM. Other transition metals like $Ca^{++}$ or $Fe^{++}$ can also be used for this purpose.

In some embodiments, the depolymerized compound can be exposed to pH range of 8 to 10 for 10 to 30 minutes at temperature of 2 to 60° C. to initiate controlled partial demethoxylation to generate a selectively middle depolymerized compound with a degree of methoxylation of 40 to 70 percent in comparison to initial levels of about 87%. The resulting compound can be referred as middle-methoxylated compound. Complete methoxylation of galacturonic acid is considered to be approximately DE 87%.

In some embodiments, the selectively-depolymerized polysaccharide of the present invention can have an endotoxin level of no more than 100 EU or no more than 300 EU as assessed by LAL method.

In some embodiments, the selectively-depolymerized polysaccharide of the present invention can have no more than 0.05% Nitrogenous impurities, as assessed by total nitrogen.

In some embodiments, the depolymerized composition can be exposed to multiple washes of hot acidic alcohol (30-80° C.) to remove any residual endotoxin, copper and heavy metals, agricultural contaminates and other impurities.

Uses

In some embodiments, the therapeutic activity of the compound of the invention can be derived from multiple beta-galactose and arabinose moieties present on the compound. Such moieties can mimic cellular glycoproteins on cell surfaces and the extracellular matrix that bind to galectin proteins (e.g. galactose-binding proteins) which are highly expressed in inflammatory, fibrogenic, and tumorgenic processes. The expression of galectin-3 has been proven to be critical to inflammation and fibrogenesis in multiple organs, including but not limited to liver, kidney, heart, and lung. Modulating their activity may thus lead to inhibition and reversing of pathologic processes.

In another embodiment, the selectively-depolymerized polysaccharide of the present invention has no cytotoxicity and does not induce apoptosis in cell culture systems. As such, the selectively-depolymerized polysaccharide of the present invention differs from other known preparations of modified pectins that have been reported (See U.S. Pat. No. 8,128,966).

In another embodiment, the selectively-depolymerized polysaccharide of the present invention can have an anti-inflammatory effect on peripheral blood mononuclear cells (PMBC) and other inflammatory cell lines. For example, Compound G can reduce expression or response to inducers of cytokine genes or proteins, including but not limited to, TNF-alpha. The process of inflammation and repair can involve multiple cell types including cells of the immune system and many inflammatory mediators in a complex and interconnected cascade of events. Acute inflammation can be terminated or can progress to a chronic phase which may lead to fibrosis, a late stage of damage seen in a variety of human organ disease including but not limited to liver, lung, kidney, heart and pancreas.

Chronic inflammation in organs often leads to an accumulation of fibrotic tissue. In fact, the end result of inflammation from multiple underlying etiologies is generally fibrosis and resultant organ dysfunction. This is evident in, for example, lung, heart, kidney, pancreas, and liver. Multiple lines of evidence point to galectin proteins, and galectin-3 in particular, as critical factors in the pathogenesis of organ fibrosis. It has, for example, been shown that Galectin-3 knock out null mice are resistant to fibrosis of the liver in response to hepatotoxins, resistant to lung fibrosis in response to intra-tracheal bleomycin, and can be used as models of kidney fibrosis, heart fibrosis, and chronic pancreatitis (Henderson et al., "The regulation of inflammation by galectin-3," Immunol Rev. 230: 160-171, 2009, Iacobini et al., "Galectin-3 ablation protects mice from diet-induced NASH: a major scavenging role for galectin-3 in liver." J. Hepatol. 54: 975-983, 2011, Lopez et al., "Gene expression profiling in lungs of chronic asthmatic mice treated with galectin-3: downregulation of inflammatory and regulatory genes," Mediators Inflamm., 823279. Epub 2011, Kolatsi-Joannou et al., "Modified citrus pectin reduces galectin-3 expression and disease severity in experimental acute kidney injury," PLoS One. 6(4): e18683, 2011).

"Fibrosis" refers to any tissue disorder, including, but not limited to, such cellular disorders as, for example, cirrhosis, kidney fibrosis, liver fibrosis, ovarian fibrosis, lung fibrosis, gastrointestinal or stomach fibrosis, and fibroids. The term "fibrosis" refers to both the pathological process leading from tissue injury through its encapsulation by extracellular matrix, and the result of the process, which is a pathological formation of scar tissue.

"Cirrhosis" refers to any tissue disorder, including such cellular disorders including, but not limited to, renal cirrhosis, liver cirrhosis, ovarian cirrhosis, lung cirrhosis, gastrointestinal or stomach cirrhosis. The term "cirrhosis" refers to an advanced stage of fibrosis, defined by the presence of encapsulated nodules. For purposes of this specification and claims, "cirrhosis" is considered to be a type of fibrosis, and is included within the meaning of the term "fibrosis" used herein.

As used herein, "molecular markers", "biochemical markers", "biomarkers", or "markers" are used interchangeably and refer to individual molecules of biological origin, which can be monitored as a "readout" of specific metabolic events. These events are accompanied by formation of the "markers", the quantitative level of which can often be used as an indication to advancement of the event.

Injury leading to fibrosis in the liver can occur in response to a variety of chronic insults, including but not limited to, alcohol abuse, drugs, toxins, fat deposition, viral hepatitis B and C, some metabolic diseases causing chronic and/or permanent tissue irritation leading to inflammation and deposition of collagen, or fibrosis.

The advanced stage of liver fibrosis is cirrhosis, defined by the presence of hepatocellular nodules encapsulated by broad bands of fibrous tissue. Fibrosis is a systematic and coordinated response to chronic injury, developing through a series of highly coordinated molecular events, collectively called fibrogenesis. For example, fibrosis can develop as a result of chronic mammalian liver injury. The steps immediately following chronic liver injury can result in the activation of hepatic stellate cells. The stellate cells' activation can lead to proliferation, fibrogenesis and cirrhosis. The activation events in stellate cells can be identified by specific molecular markers, such as collagen I, alpha 1-smooth muscle actin, beta PDGF-receptor (a proliferation biomarker), matrix metalloproteinases and their inhibitors MMP2, MMP9, TIMP1 and TMP2 (markers on matrix degradation), and a variety of cytokines, including but not limited to, TFG-beta1 (a marker of fibrogenesis). Development of fibrosis can be evaluated by the quantitative level of the respective markers. Reduction of fibrosis can be evaluated by the decrease of the level of the respective markers during various stages of fibrosis.

The pathophysiologic spectrum of fibrosis may be associated with serum biomarkers including but not limited to hyaluronic acid and other breakdown products of collagens, cytokeratin-18 and other cytoskeletal cellular proteins, tissue inhibitor of metalloprotease I and II, other liver derived collagen, matrix proteases or combinations thereof. These compounds and/or biomarkers may be measured in serum or liver tissue using immunoassays and the levels correlated with severity of disease and treatment.

The pathophysiologic spectrum of fibrosis also may be associated with serum biomarkers, including, but not limited to, reactive oxygen products of lipid or protein origin, lipid molecules or conjugates, or combinations thereof. These biomarkers can be measured by various means including immunoassays and electrophoresis and their levels correlated with severity of disease and treatment. Additional biomarkers may include global shifts in proteomic analysis of serum or urine proteins.

The pathophysiologic spectrum of fibrosis also may be associated with serum biomarkers of NASH, a chronic metabolic inflammatory disorder that leads to fibrosis and is described in this application. These biomarkers can be cytokines, including but not limited to, TNF-alpha, TGF-beta or IL-8, or a metabolic profile of serum components that is indicative of NASH presence or severity (these include serum and urine markers) or combinations thereof. A profile of one or more of the cytokines biomarkers, as measured by immunoassay or proteomic assessment by LC mass spec, may provide an assessment of activity of the disease and a marker to follow in therapy of the disease.

The pathophysiologic spectrum of fibrosis in the liver also may be associated with histopathological findings on liver biopsy, that include but are not limited to, evidence of collagen deposition (including but not limited to peri-sinusoidal, portal, central collagen deposition or combinations thereof), portal to central bridging collagen deposition, hepatocellular nodules that distort the normal architecture, hepatocellular atypia consistent with malignant transformation or combinations thereof.

The pathophysiologic spectrum of fibrosis in the liver may also be associated with other pathological histological findings on liver biopsy that are associated with the underlying cause of chronic liver disease that results in fibrosis. Such findings can include, but are limited to, abnormalities in hepatocytes (including, but not limited to, ballooning degeneration and intracellular hyaline and macrovesicular or microvesicular fat or combinations thereof), endothelial cells, macrophages, or bile duct cells and the infiltration of multiple types of inflammatory cells, such as lymphocytes, monocytes, and/or neutrophils, or any combination of the foregoing.

The pathophysiologic spectrum of fibrosis can also include histopathological findings on liver biopsy that are related to the underlying disease of NASH. Such findings can include, but are not limited to, evidence of intra-hepatocellular fat, hepatocellular toxicity including but not limited to hyaline bodies, inflammatory cell infiltrates (including but not limited to lymphocytes and various subsets of lymphocytes and neutrophils), changes in bile duct cells, changes in endothelial cells, number of Kupffer cell macrophages, collagen deposition (including but not limited to peri-sinusoidal, portal and central collagen deposition and portal to central bridging collagen deposition, hepatocellular nodules that distort the normal architecture, hepatocellular atypia consistent with malignant transformation, and various scales and methods that combine various sets of observations for grading the severity of NASH or any combinations of the foregoing. Such histological assessments can be the sine-qua-none of NASH diagnosis and therefore can integrally relate to assessment of therapy.

The pathophysiologic spectrum of fibrosis can also include histopathological findings on liver biopsy that examine the expression of or change in expression of various molecules and their localization in liver tissue or various cell types. Suitable molecules include, but are not limited to, various cytokine proteins. Cytokine proteins of interest can include, but are not limited to, TGF-beta, inflammatory mediators, reactive metabolite scavenger transport proteins, including but not limited to, CD36, and galectin proteins, including but not limited to galectin-3 protein, or any combinations of the foregoing.

Clinical manifestations of fibrosis can include, but are not limited to, clinical testing of stage and severity of the disease, clinical signs and symptoms of disease, and/or medical complications resulting from fibrosis. Clinical testing of stage and severity of liver fibrosis can include, but are not limited to, hematologic testing (including, but not limited to, red blood cell count and/or morphology, white blood cell count and/or differential and/or morphology, and/or platelet count and morphology), serum or plasma lipids, including but not limited to, triglycerides, cholesterol, fatty acids, lipoprotein species and lipid peroxidation species, serum or plasma enzymes (including but not limited to aspartate transaminase (AST), alanine transaminase (ALT), alkaline phosphatase (AP), gamma glutamyltranspeptidase (GGTP), lactate dehydrogenase (LDH) and isoforms, serum or plasma albumin and other proteins indicative of liver synthetic capacity, serum or plasma levels of bilirubin or other compounds indicative of the ability of the liver to clear metabolic byproducts, serum or plasma electrolytes (including but not limited to sodium, potassium, chloride, calcium, phosphorous), coagulation profile including but not limited to prothrombin time (PT), partial thromoplastin time (PTT), specific coagulation factor levels, bleeding time and platelet function. Clinical testing also includes but is not limited to non-invasive and invasive testing that assesses the architecture, structural integrity or function of the liver including but not limited to computerized tomography (CT scan), ultrasound (US), ultrasonic elastography (FibroScan) or other measurements of the elasticity of liver tissue, magnetic resonance scanning or spectroscopy, magnetic resonance elastography, percutaneous or skinny needle or transjugular liver biopsy and histological assessment (including but not limited to staining for different components using affinity dyes or immunohistochemistry), measurement of hepatic portal-venous wedge pressure gradient, or other non-invasive or invasive tests that may be developed for assessing severity of fibrosis in the liver tissue or any combinations of the foregoing.

Clinical signs and symptoms of advanced fibrosis that has progressed to cirrhosis can include fatigue, muscle weight loss, spider angiomata, abdominal pain, abdominal swelling, ascites, gastrointestinal bleeding, other bleeding complications, easy bruising and ecchymoses, peripheral edema, hepatomegaly, nodular firm liver, somnolence, sleep disturbance, confusion, and/or coma. Medical complications of fibrosis are related to cirrhosis and include ascites, peripheral edema, esophageal and other gastrointestinal tract varices, gastrointestinal bleeding, other bleeding complications, emaciation and muscle wasting, hepatorenal syndrome, and hepatic encephalopathy. An additional complication of fibrosis related cirrhosis is the development of complications sufficiently severe to warrant placement on liver transplantation list or receiving a liver transplantation.

Nonalcoholic fatty liver disease (NAFLD) and steatohepatitis (NASH) are common liver disorders in the United States and Europe. Histopathologically, these disorders resemble alcoholic liver disease, but can occur in people who drink little or no alcohol. The pathological changes in the liver include, but are not limited to, fat accumulation in hepatocytes, evidence of hepatocellular degeneration, infiltrates of inflammatory cells, deposition of excess fibrous tissue, hepatocellular nodule formation, cirrhosis, hepatocellular carcinoma and combinations thereof.

The major feature in NAFLD is fat accumulation in hepatocytes with minimal inflammation. NAFLD is usually identified on the basis of a liver biopsy performed because of mildly elevated liver transaminase levels in the patient's serum or the suspicion of fatty liver on non-invasive testing such as computerized tomography or ultrasound.

A subset of individuals with NAFLD are found to have NASH, which is fatty liver with the addition of the development of infiltration of inflammatory cells (including but not limited to neutrophils or lymphocytes) within the lobule, central vein and portal areas and evidence of damage to hepatocytes, including but not limited to, ballooning degeneration. This inflammatory state of NASH may result in the deposition of fibrous tissue, including but not limited to, collagen, which can lead to cirrhosis, nodule formation, and/or hepatocellular carcinoma.

The disease progress is insidious since most people with NASH feel well and are not aware that they have a liver problem. Despite the lack of symptoms, NASH can be severe and can lead to the deposition of fibrotic material in the liver which can result in severe scarring and/or cirrhosis and, in some cases, hepatocellular carcinoma.

The cause of liver injury in NASH is not known. Multiple theories have been proposed, with some experimental data to suggest their involvement. Some of these include, but are not limited to, hepatocyte resistance to the action of insulin, production of inflammatory cytokines by fat cells and other inflammatory cells that damage the liver and recruit additional inflammatory cells and oxidative stress in hepatocytes with production of reactive oxygen radicals that damage liver cells and induce inflammation.

To date no specific therapies for NASH or fibrosis exist and only general health recommendations are currently provided to patients. These include weight reduction, eating a balanced and healthy diet, increasing physical activity, and avoidance of alcohol and unnecessary medications. Weight loss can improve serum liver tests in some patients with NASH and may improve evidence of histological liver damage, but it does not reverse severe liver disease. In addition, it should be noted that not all patients with NASH are overweight.

A variety of experimental approaches have been evaluated, or are under evaluation in patients with NASH or fibrosis including, but not limited to administration of antioxidants, such as vitamin E, selenium, betaine, and antidiabetic agents including metformin, rosiglitazone, and pioglitazone. All clinical results to date have been disappointing. In some embodiments, the compound of the present invention may be used in the treatment of NASH or fibrosis. The compound of the present invention may be effective through manipulation of galectin proteins that are involved in pathogenesis and progression of diseases.

In some embodiments, the compound of the present invention (i.e. Compound G) has a clinically significant effect on fatty-liver metabolism in addition to fibrosis, whereas it may have a more of a clinically significant effect on related pathologies in addition to inflammation and fibrosis.

Figure 13:
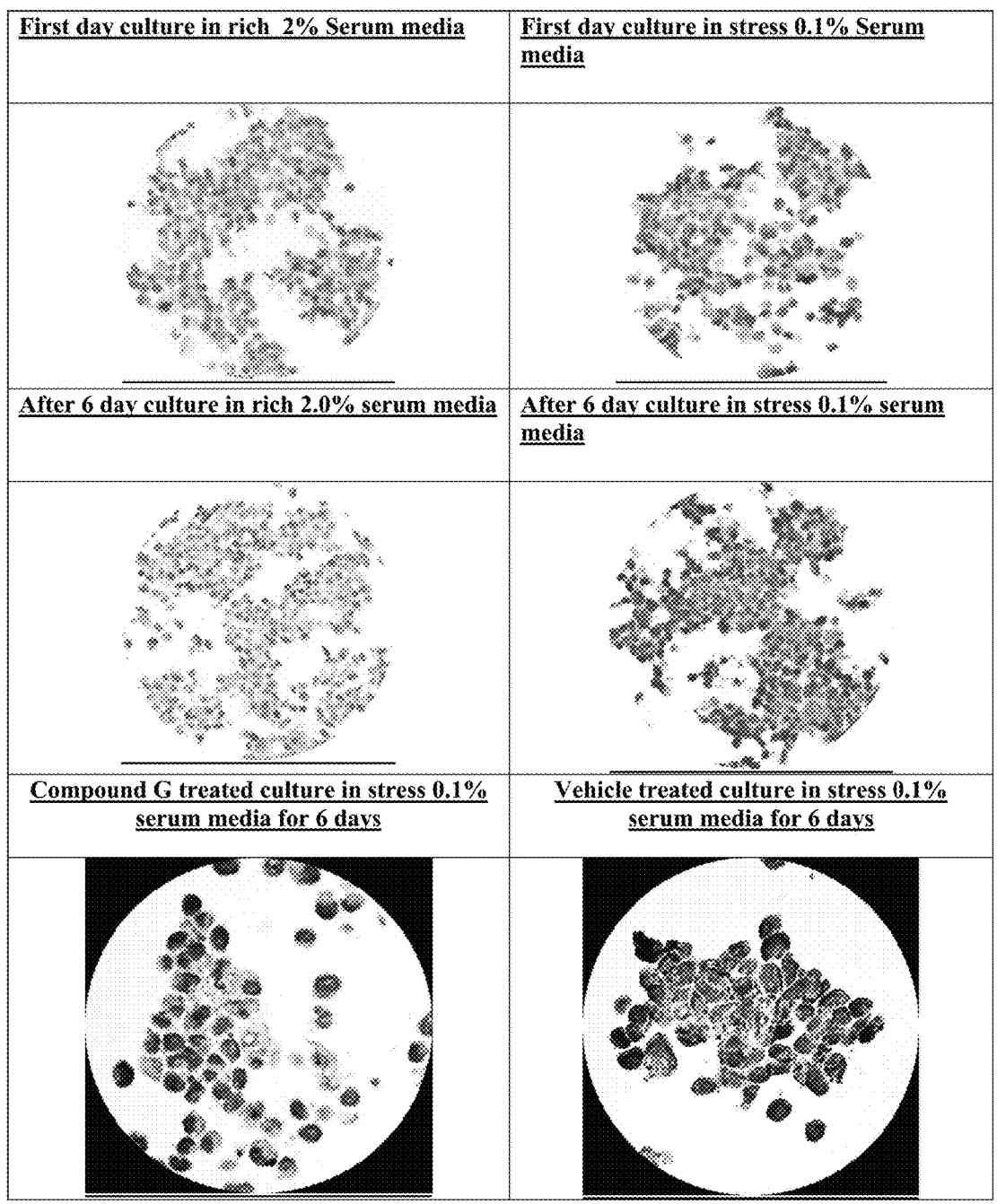
FIG. 13 is a photograph of immunostaining of galectin-3 with MAb-HRP depicting the anti-galectin suppression effect of Compound G on secretion of galectin-3 by LX-2 cells.
Figure 14:
FIG. 14 is a depiction of an experimental rat fibrosis model induced by thioacetamide injection (TAA model, a chemical toxicity liver fibrosis model).
Figure 14:
Figure 14:
Figure 14:

In some embodiments, the compound of the present invention has an anti-fibrotic effect in rat fibrosis model where fibrosis is induced by chemical toxin thioacetamide (TAA) which have similar pathology to the effect of chronic consumption of alcohol that lead to fibrosis, cirrhosis and increase occurrence of hepatocarcinoma. (FIGS. 13-14)

Figure 16:
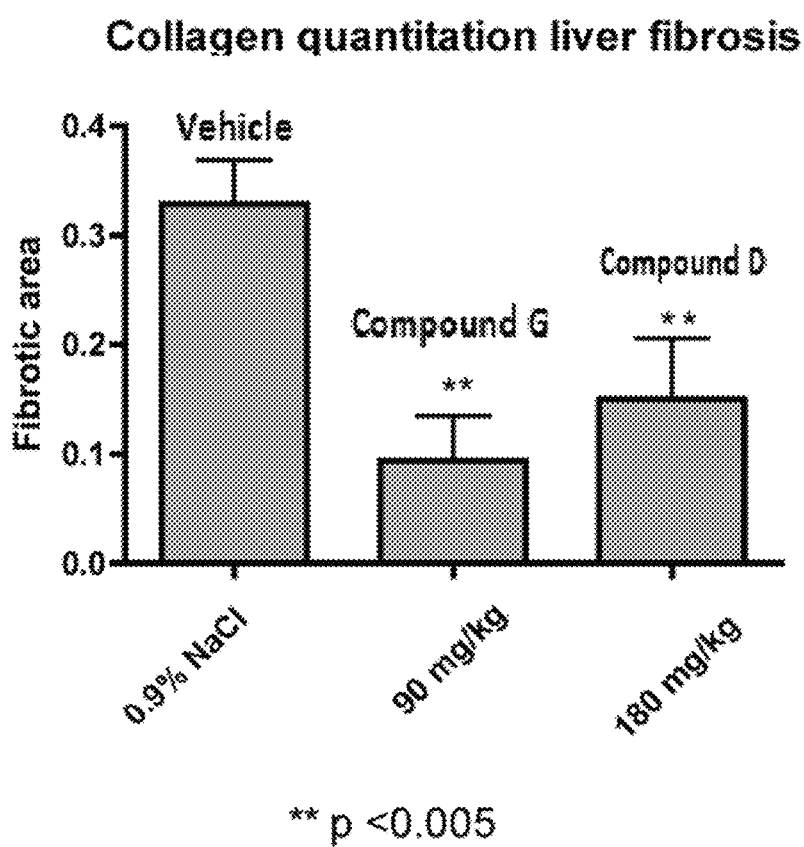
FIG. 16 is a graphical and statistical comparison of percentage of collagen in liver (as a measure of fibrosis) in the TAA model after 4 weekly treatments with vehicle control, Compound D and Compound G. Sirius Red staining was used for quantitative measurement of percent collagen in the histological slides.

In some embodiments, the compound of the present invention has an anti-inflammatory effect by reducing secretion of TNF alpha as depicted in an in-vitro model using PBMC cell stressed with microbial endotoxin to produce TNF alpha, a major cytokine, a biomarker and an inflammatory protein (FIG. 16).

Based on this discovery, the Compound G is proposed as therapy alone or in combination with other compounds listed above as treatment for human NASH. In some embodiments, the compound of the present invention can be used for ameliorating or reversing hepatocyte fat accumulation, intra-portal and intra-lobular inflammatory infiltrate, and/or fibrosis, including but not limited to collagen deposition in the peri-sinusoidal space, cirrhosis, and for preventing progression to hepatocellular carcinoma.

In addition to NASH, there are multiple other chronic liver diseases that result in fibrosis and can progress to cirrhosis. For example, chronic liver diseases can include, but are not limited to, chronic hepatitis virus infection (hepatitis B, C, and D), chronic alcohol abuse, biliary diseases (including, but not limited to, sclerosing cholangitis), primary biliary cirrhosis, genetic storage diseases, and metal storage diseases (including but not limited to hemochromatosis and Wilsons disease).

In some embodiments, Compound G may be effective in all chronic liver diseases that lead to fibrosis regardless of the underlying etiology.

In some embodiments, Compound G may be effective in the treatment of fibrosis in organs other than the liver, including, but not limited to, lung, kidney, heart and pancreas occurs through chronic inflammation leading to collagen deposition by cell types other than stellate cells which are specific to the liver. The cells responsible for fibrosis in other organs are myofibroblasts that have precursor cells that include, but are not limited to, resident tissue fibroblasts, circulating fibrocytes, or epithelial cells generated through a process called EMT—epithelial mesenchymal transformation.

Lung fibrosis can occur as a result of chronic inflammatory process in a variety of diseases including, but not limited to, idiopathic pulmonary fibrosis, chronic obstructive lung disease, and chronic infections.

Fibrosis in the lung usually leads to stiffness of the lung tissues resulting in reduced function of the lung, including but not limited to, reduced total lung capacity, vital capacity, forced expiratory volume, and diffusion capacity. These reduced functions can lead to clinical symptoms, including but not limited to, shortness of breath, reduced exercise tolerance, and reduced gas exchange resulting in low blood oxygen levels. The ultimate result can be lung failure which requires a lung transplant. There are no current pharmacological therapies for lung fibrosis.

Kidney fibrosis can occur as a result of multiple underlying diseases, including but not limited to, diabetes, obstruction of the urinary tract, hypertension, vascular disease, and autoimmune diseases.

Kidney fibrosis can progress to inhibit kidney function which results in reduced urine output and the accumulation of toxic metabolites in the blood stream. Kidney failure associated with kidney fibrosis requires external support through dialysis or a kidney transplant. There are no known current pharmacological therapies for kidney fibrosis.

Progressive heart failure is associated with multiple diseases, including but not limited to, chronic hypertension, coronary artery disease, valvular heart disease, and hypertrophic heart disease. Heart failure can occur in part because of the deposition of fibrous tissue in the heart muscle, a process that has been shown to be associated causally with an increased expression of galectin-3. Progressive heart failure can result in reduced contractility of the heart, dilation of the heart chambers, reduced cardiac output with multiple resultant symptoms including edema, shortness of breath, reduced kidney function, mental confusion, and others. In the end stage, heart failure can only be treated with mechanical cardiac assist devices or heart transplantation.

Chronic inflammation of the pancreas due most commonly, but not exclusively, to alcohol abuse, can result in fibrosis of the pancreas and reduced function of the exocrine and endocrine pancreas. Reduced exocrine function can lead to malabsorption of food and reduced endocrine function can lead to endocrine disorders, such as diabetes. To date, there are no pharmacological therapies for pancreas fibrosis.

Galectin proteins have been shown to have multiple functions in cancer cells including, but not limited to, enhancing invasiveness, causing resistance to chemotherapy, promoting metastasis, enhancing neovascularization, and allowing evasion of the immune system.

The vast majority of cancers express increased amounts of galectin proteins. Inhibition of galectins via administration of the compound of the present invention (e.g. Compound G) may be efficacious in therapy of cancers that express galectins including but not limited cancers of the skin (squamous and melanoma), mouth, head and neck, lymphatic system, blood cells, alimentary tract (esophagus, stomach, small intestine, colon and rectum), pancreas, biliary tree, liver, lung, breast, kidney, ovary, testes, cervix, uterus, and neurological system Aspects of the invention relate to a compound, or a composition comprising the compound, utilized for the treatment of inflammatory and fibrotic disorders in which galectins are involved in the pathogenesis, including but not limited to enhanced anti-fibrosis activity in organs, including but not limited to liver, kidney, lung, and heart. Other aspects of the invention relate to the methods of treating inflammatory and fibrotic disorders in which galectins are involved in the pathogenesis.

In some embodiments, the invention relates to a compound, a composition that has therapeutic activity or a method to reduce the pathology and disease activity associated with nonalcoholic steatohepatitis (NASH) including, but not limited to, steatosis (fat accumulation in hepatocytes), ballooning degeneration of hepatocytes, inflammatory infiltrate in the liver, and deposition of collagen or fibrosis.

In some embodiments, the invention relates to a compound, or a composition comprising the compound, utilized in treating inflammatory and autoimmune disorders in which galectins are involved in the pathogenesis including, but not limited to, arthritis, rheumatoid arthritis, asthma, and inflammatory bowel disease (ulcerative colitis and Crohn's Disease).

In some embodiments, the invention relates to a compound, or a composition comprising the compound, utilized in treating neoplastic conditions (e.g. cancers) in which galectins are involved in the pathogenesis by inhibiting processes promoted by the increase in galectins, including, but not limited to, tumor cell invasion, metastasis, and neovascularization.

In some embodiments, the invention relates to a compound, or a composition comprising the compound, utilized in enhancing or a method for enhancing the ability of tumor infiltrating T-cells, which are inhibited by the effect of tumor derived galectin proteins, to more effectively identify and kill tumor cells and thereby slow, stop or reverse the progression of tumors.

In some embodiments, the invention relates to a compound, a composition comprising the compound utilized in combination with tumor immunotherapy which may be a vaccine directed towards specific tumor antigens or agents which activate or inhibit specific immune regulatory molecules including but not limited to CTLA4, OX40, PD-1, or PD-L.

An effective dose of the compound of the present invention or a composition comprising an effective dose of the compound can be administered via a variety of routes including, parenteral via an intravenous infusion given as repeated bolus infusions or constant infusion, intradermal injection, subcutaneously given as repeated bolus injection or constant infusion, intra-articular injection, inhaled in an appropriate formulation, or oral administration.

The amount administered depends on the compound formulation, route of administration, etc. and is generally empirically determined in routine trials, and variations will necessarily occur depending on the target, the host, and the route of administration, etc.

"Administration" refers to oral, or parenteral including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection and infusion.

An effective parenteral dose of the compound of the present invention to an experimental animal can be within the range of 2 mg/kg up to 200 mg/kg body weight given intravenously. An effective subcutaneous injection dose of the compound of the present invention to an animal can be within the range of 2 mg/kg up to 200 mg/kg body weight, or by intraperitoneal 2 mg/kg up to 200 mg/kg or by oral administration 10 mg/kg or 50 mg/kg or 200 mg/kg or 1500 mg/kg body weight. Higher and lower doses can also be contemplated.

An effective parenteral dose of the compound of the present invention to a human subject can be within the range of 0.2 mg/kg up to 20 mg/kg body weight given intravenously. An effective subcutaneous injection dose of the compound of the present invention to a human subject can be in the range of 0.2 mg/kg up to 50 mg/kg body weight or by oral administration 10 mg/kg up to 200 mg/kg body weight. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective parental dose may be given daily (in one or divided doses), three times weekly, two times weekly, or monthly via intravenous, intradermal, subcutaneous or other routes as practiced by the medical professional to administrate drugs.

An effective oral dose of the compound of the present invention to an experimental animal or human may be formulated with a variety of excipients and additives that enhance the absorption of the compound via the stomach and small intestine.

An effective oral dose could be 10 times and up to 100 times the amount of the effective parental dose.

An effective oral dose may be given daily, in one or divided doses or twice, three times weekly, or monthly.

The compound of the present invention or compositions comprising the compound of the present invention may be administered orally; or by intravenous injection; or by injection directly into an affected tissue, as for example by injection into an arthritic joint. In some instances the compound or composition may be administered topically, as in the form of eye drops, nasal sprays, ointments or the like. Also, other techniques such as transdermal delivery systems, inhalation or the like may be employed.

In some embodiments, the compounds described herein can be co-administered with one or more other therapeutic agents. In certain embodiments, the additional agents may be administered separately, as part of a multiple dose regimen, from the compounds of this invention (e.g., sequentially, e.g., on different overlapping schedules with the administration of the compound of the invention. In other embodiments, these agents may be part of a single dosage form, mixed together with the compounds of this invention in a single composition. In still another embodiment, these agents can be given as a separate dose that is administered at about the same time that the compound of the invention. When the compositions include a combination of the compound of this invention and one or more additional therapeutic or prophylactic agents, both the compound and the additional agent can be present at dosage levels of between about 1 to 100%, and more preferably between about 5 to 95% of the dosage normally administered in a monotherapy regimen.

In some embodiments, a therapeutically effective amount of the depolymerized compound or of the composition can be compatible and effective in combination with a therapeutically effective amount of various anti-oxidant compounds (e.g. glycyrrhizin, ascorbic acid, L-glutathione, cysteamine etc) as described in U.S. Pat. No. 7,078,064.

An effective dose given to an animal or human subject with NASH and liver fibrosis means the amount of a compound that, alone or in combination with amount of other therapeutic agent, when administered as a parental, subcutaneous, inhaled, intra-articular, ocular, or oral formulation results in at least a 10% reduction in hepatocellular fat, hepatocytes with ballooning degeneration, inflammatory cell infiltrated, at least a one point reduction in the NAFLD activity score, or at least a 10% reduction in collagen deposition in the liver assessed by histological staining with Sirius red, or slowing the progression of deposition of fibrotic tissue in the liver by at least 10%.

An effective dose given to a human subject with NASH and liver fibrosis can result in at least a 10% reduction in serum biomarkers associated with NASH, or at least a 10% improvement in hepatocyte fat content or liver stiffness as assessed by ultrasound or MR elastography, or at least a 10% improvement in liver function tests that measure metabolic function or shunting in the liver, or at least a 10% reduction in clinical symptoms and complications resulting from liver fibrosis and cirrhosis including but not limited to symptoms and complications resulting from reduced metabolic and elimination processes (including but not limited to bilirubin), reduced liver synthetic capacity (including but not limited to albumin and coagulation proteins), portal hypertension, and hepatic encephalopathy.

An effective dose given to a human subject with NASH and liver fibrosis means an improvement in clinical parameters or reduced progression of clinical parameters when compared to a control untreated group of human subjects including but not limited to at least a 10% reduction in serum biomarkers associated with NASH, or at least a 10% improvement in hepatocyte fat content or liver stiffness as assessed by ultrasound or MR elastography, or at least a 10% improvement in liver function tests that measure metabolic function or shunting in the liver, or at least a 10% reduction in clinical symptoms and complications resulting from liver fibrosis and cirrhosis including but not limited to symptoms and complications resulting from reduced metabolic and elimination processes (including but not limited to bilirubin), reduced liver synthetic capacity (including but not limited to albumin and coagulation proteins), portal hypertension, and hepatic encephalopathy.

An effective dose given to an animal or human subject with liver fibrosis or cirrhosis due to a disorder other than NASH means the amount of a compound that, alone or in combination with amount of other therapeutic agent, when administered as a parental, subcutaneous, inhaled, intra-articular, ocular, or oral formulation results in, for example, at least a 10% reduction in collagen deposition in the liver assessed by histological staining with Sirius red, or slowing the progression of deposition of fibrotic tissue in the liver by at least 10%.

An effective dose given to a human subject with liver fibrosis or cirrhosis due to a disorder other than NASH means the amount of a compound that, alone or in combination with amount of other therapeutic agent, when administered as a parental, subcutaneous, inhaled, intra-articular, ocular, or oral formulation results in, but is not limited to, at least a 10% reduction in serum biomarkers associated with liver fibrosis, or at least a 10% improvement in liver stiffness as assessed by ultrasound or MR elastography, or at least a 10% improvement in liver function tests that measure metabolic function or shunting in the liver, or at least a 10% reduction in clinical symptoms and complications resulting from liver fibrosis and cirrhosis including but not limited to symptoms and complications resulting from reduced metabolic and elimination processes (including but not limited to bilirubin), reduced liver synthetic capacity (including but not limited to albumin and coagulation proteins), portal hypertension, and hepatic encephalopathy.

An effective dose given to a human subject with liver fibrosis or cirrhosis due to a disorder other than NASH means an improvement in clinical parameters or reduced progression of clinical parameters when compared to a control untreated group of human subjects including but not limited to at least a 10% reduction in serum biomarkers associated with fibrosis, or at least a 10% improvement in liver stiffness as assessed by ultrasound or MR elastography, or at least a 10% improvement in liver function tests that measure metabolic function or shunting in the liver, or at least a 10% reduction in clinical symptoms and complications resulting from liver fibrosis and cirrhosis including but not limited to symptoms and complications resulting from reduced metabolic and elimination processes (including but not limited to bilirubin), reduced liver synthetic capacity (including but not limited to albumin and coagulation proteins), portal hypertension, and hepatic encephalopathy.

An effective dose given to an animal or human subject with kidney fibrosis means an improvement in clinical parameters or reduced progression of clinical parameters when compared to a control untreated group of animals or human subjects including but not limited to at least a 10% reduction in kidney fibrosis assessed by histology, or a least a 10% improvement in proteinuria, or at least a 10% improvement in glomerular filtration rate, or at least a 10% improvement in clinical signs and symptoms related to renal insufficiency.

An effective dose given to an animal or human subject with lung fibrosis means an improvement in clinical parameters or reduced progression of clinical parameters when compared to a control untreated group of animals or human subjects including but not limited to at least a 10% reduction in lung fibrotic tissue assessed on histology, 10% improvement in lung volumes, or at least a 10% improvement in expiratory volumes, or at least a 10% improvement in clinical signs and symptoms related to pulmonary insufficiency.

An effective dose given to an animal or human subject with heart fibrosis means an improvement in clinical parameters or reduced progression of clinical parameters when compared to a control untreated group of animals or human subjects including but not limited to at least a 10% reduction in heart fibrotic tissue assessed on histology, 10% improvement in heart contractility, or at least a 10% improvement in cardiac output, or at least a 10% improvement in clinical signs and symptoms related to heart failure.

An effective dose given to an animal or human subject with pancreatic fibrosis means an improvement in clinical parameters or reduced progression of clinical parameters when compared to a control untreated group of animals or human subjects including but not limited to at least a 10% reduction in pancreas fibrotic tissue assessed on histology, 5% improvement in synthesis or secretion of pancreatic exocrine enzymes, or at least a 5% improvement in pancreatic endocrine enzymes including but not limited to insulin, or at least a 10% improvement in clinical signs and symptoms related to pancreatic insufficiency.

An effective dose given to an animal or human subject with cancer, either as a single agent or in combination with other cancer chemotherapy, immunotherapy, or tumor vaccines, means an improvement in clinical parameters or reduced progression of clinical parameters when compared to a control untreated group of animals or human subjects including but not limited to at least a 10% reduction in size of tumors, or at least a 10% reduction in number of cancer metastases, or at least a 10% increase in activity of immune system against the cancer cells, or at least a 10% improvement in clinical signs and symptoms related to cancer including but not limited to improvement in progression free survival, or overall survival, or reduced adverse effects of therapy, or improved quality of life.

While a number of embodiments of the present invention have been described, it is understood that these embodiments are illustrative only, and not restrictive, and that many modifications and/or alternative embodiments may become apparent to those of ordinary skill in the art. For example, any steps may be performed in any desired order (and any desired steps may be added and/or any desired steps may be deleted). Therefore, it will be understood that the appended claims are intended to cover all such modifications and embodiments that come within the spirit and scope of the present invention.

The invention will be further described in the following examples. It should be understood that these examples are for illustrative purposes only and are not to be construed as limiting this invention in any manner.

EXAMPLES

For reference, the selectively depolymerized product of the instant invention (Compound G) refers to a compound prepared in accordance with Example 1 described herein, Compound D refers to a reference polysaccharide prepared in accordance with the methods disclosed in U.S. Pat. No. 7,893,252, incorporated herein by reference in its entirety. Compound H refers to a high molecular depolymerized pectin polysaccharide (90,000 to 140,000 D), one not prepared in accordance with Example 1 described herein, but rather prepared according with the methods disclosed in U.S. Pat. No. 8,236,780, incorporated herein by reference in its entirety. Compound S refers to a polysaccharide manufactured from USP Citrus pectin according to the methods disclosed in U.S. Pat. No. 8,128,966. The invention provides manufacturing process of modified pectin, and use in cancer treatment. And it is incorporated herein by reference in its entirety. Compound T refers to a commercial MCP "Thorne Research Fractionated Pectin Powder 5 OZ" purchased on Amazon.com.

Example 1: Manufacturing of Compound G

The selectively depolymerized product of the instant invention was prepared by a process illustrated in FIG. 1.

Apple pectin USP HM (50 kg) was dissolved and heated in water to 35-85° C. 1 M HCl or NaOH was added in order to pH-adjust the solution to pH 5-7 and mixed well. The mixing was continued for 2 hours at the 35-85° C. set-point. 1M NaOH or HCl was added as needed to readjust pH to between 5 and 7. Solution was cooled to 30° C. At 30° C., pH was adjusted to between 5 and 7.

$CuSO_4$ is added to the pH-adjusted pectin solution so as to result in a final 1 mM $CuSO_4$ concentration. The 1 mM $CuSO_4$ solution was mixed for 30 minutes at a temperature of between 10° C. and 30° C.

At the conclusion of the 30 minute, 1 mM $CuSO_4$ mixing step, 50 grams sodium ascorbate was added (amount was pre-calibrated to achieve the desired MW) and mixed for 5 to 20 minutes. $H_2O_2$ was added start with 0.02 and up to 1.0 moles/kg pectin (pre-calibrated for initial starting pectin MW) and the $H_2O_2$ concentration was maintained for 4 hours (using quantitative test, Sigma, St-Louis) while the solution pH was maintained between 4 and 7.

5M NaOH was added to the solution so as to result in a solution pH of between 8 and 10. The pH-adjusted solution was mixed for 10-30 minutes. Concentrated HCL was then added to the pH-adjusted solution to adjust the pH of the solution to between 4 and 5. The solution, once adjusted to pH between 4 and 5 can be kept mixing for 2 to 24 hours between 2° C. and 8° C.

Solution was then heated to 80° C. for 30-180 minutes and 1-5 kg of Filter-Aid was added (Celite) to the solution, and the solution with added Celite was stirred for 30 minutes and then filtered. The solids resulting from the filtration were discarded.

The filtrate was concentrated 1.5-3× under vacuum, and then pH-adjusted to between 3 and 5. Hot ethanol or isopropanol was added on a 50% weight. The mixture was stirred 1-2 hours to precipitate product, and the mixture was then filtered. The filtrate was discarded, leaving a white to off-white precipitate.

Cold 96% EtOH was added to the solution and the resulting slurry was then stirred for 30 minutes. The solution was filtered and the filtrate was discarded. The 96% EtOH slurry step was repeated, followed by a final filtration and recovery of a white to off-white precipitate.

Figure 2:
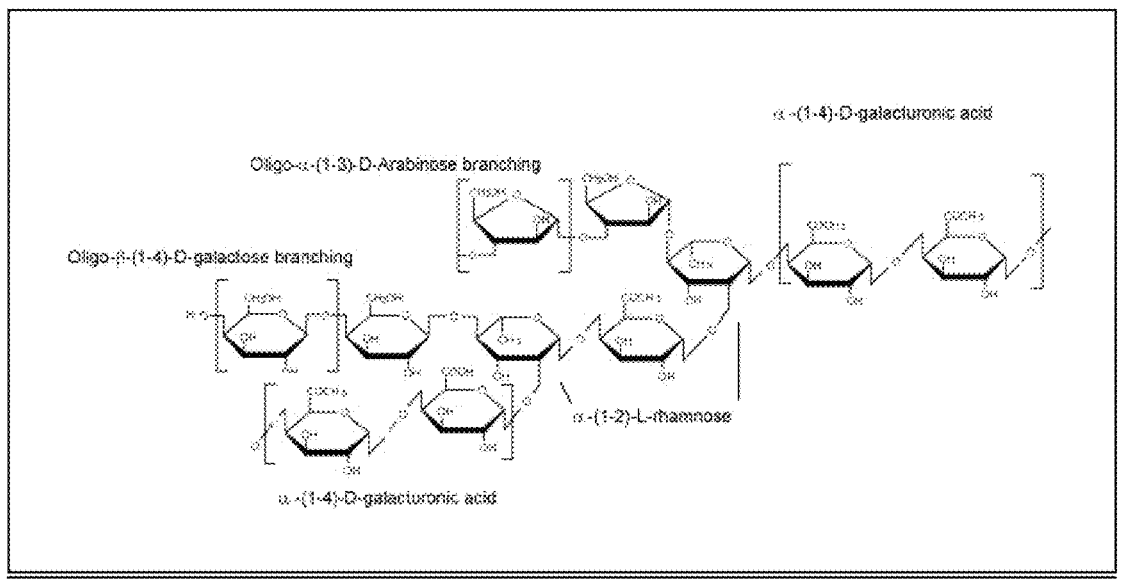
FIG. 2 shows an illustration of the molecular structure of Compound G according to some embodiments.

The final product of this process yields a composition with general the molecular structure shown in FIG. 2, as assessed by the analyses described in Examples 2, 3, 4, and 5 below.

Example 2: Analysis of Average Molecular Weight by MALLS

A Multi-Angle Laser Light Scattering detection system can be used to generate a ZIMM plot that independently predicts the molecular weight of polymers. The principle of the MALLS method is based on the fact that light is more strongly scattered by large molecules than by small molecules. The output of the light scattering detector is proportional to the multiplication of the concentration and the average molecular weight of macromolecules. Therefore, the shape of the light scattering peak is asymmetric. Molecular weight versus the elution volume is obtained and average molecular weights and average molecular weight distributions can be calculated.

Figure 3A:
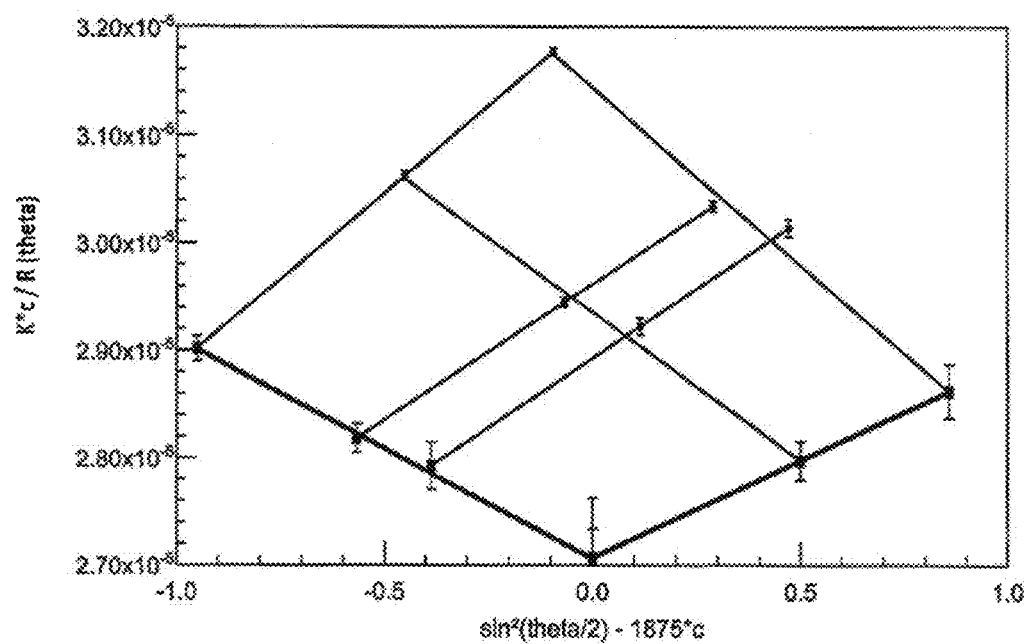
FIG. 3a shows a Zimm plot calculation of average molecular weight calculated for the selectively depolymerized compound of the instant invention (Compound G) as determined by Multi-Angel Laser Scattering Analyzer (MALS) method.
Figure 3B:
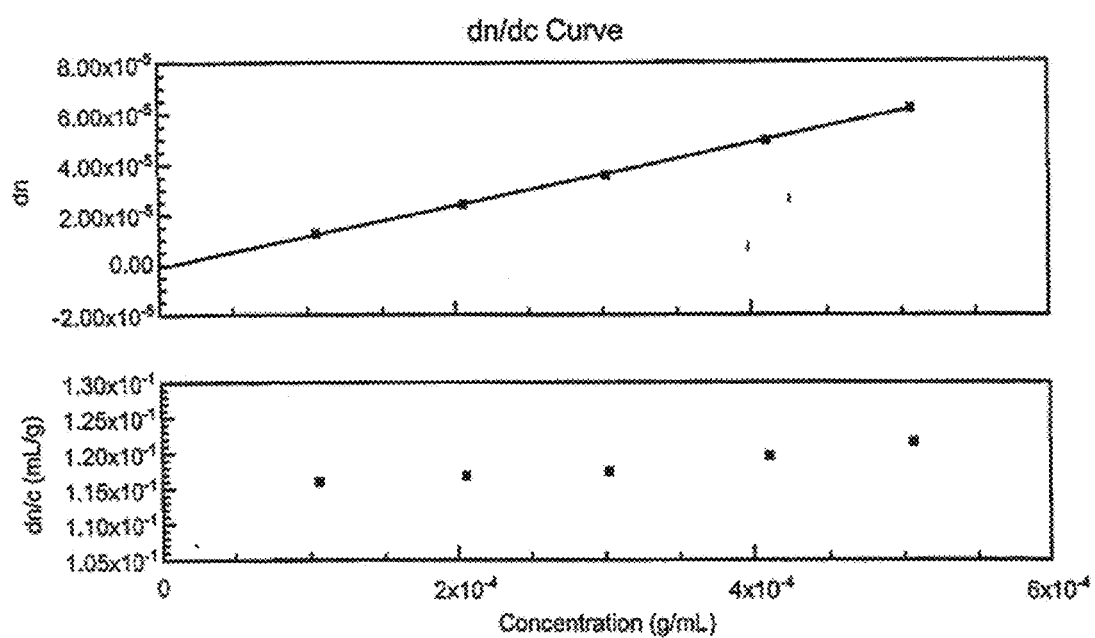
FIG. 3b shows a Zimm plot calculation of do/dc parameters calculated for the selectively depolymerized compound (Compound G) of the instant invention in a 10 nM EDTA buffered solution as determined by Multi-Angel Laser Scattering Analyzer (MALS) method.

Table 1 below and FIGS. 3A-3B illustrate a determination of the average molecular weight of a selectively depolymerized compound of the instant invention by MALLS, indicating an average molecular weight of approximately 37 kilodaltons (kD) in EDTA buffer solution with a standard deviation of 8%.

TABLE 1

| Study Number | Sample ID | Results (Daltons) |
|---|---|---|
| 3098-003 | 3098-003-00001 (EDTA) | 36,950 [STD 8%] |

Example 3: Analysis by High Performance Liquid Chromatography (HPLC)

Figure 4A:
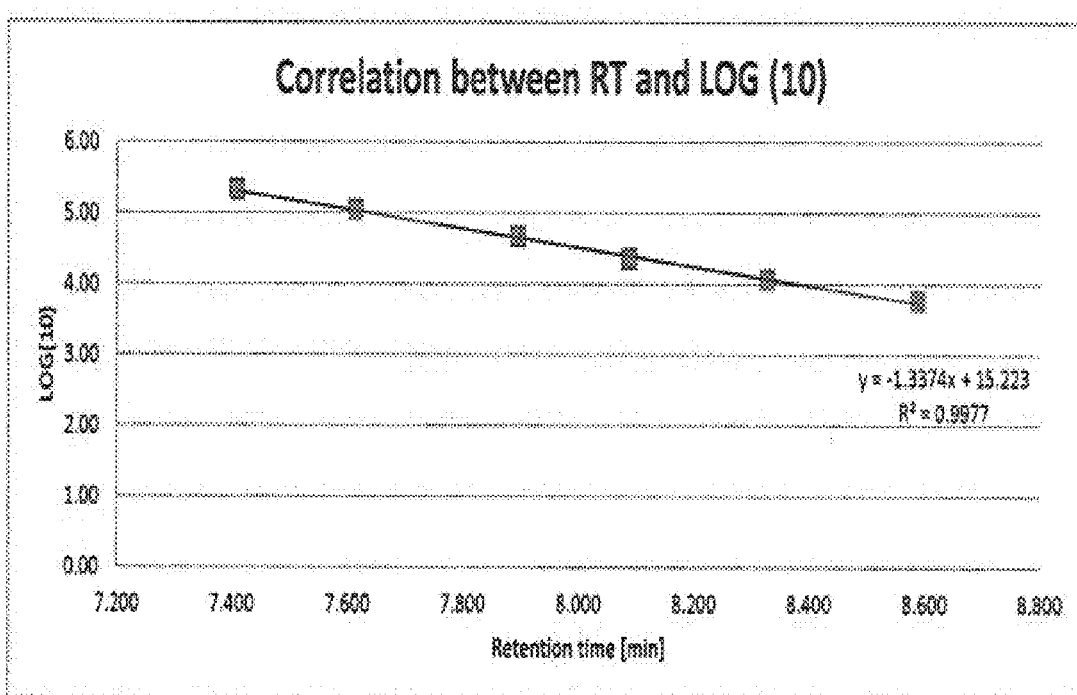
FIG. 4a shows the determination of molecular weight distribution of the selectively depolymerized compound (Compound G) of the instant invention using a size exclusion chromatography (SEC) method. The standard curve is established by reference to polysaccharides molecular weight (MW) standards monitored by Refractive Index (RI) detector which are used to calculate the average molecular weight.

Size Exclusion Chromatography (SEC) is a well-established technique using HPLC for the characterization of polymers. SEC in combination with Refractive Index (RI) detection is used for the determination of average molecular weights of polymeric carbohydrates by retention time profile. FIG. 4a demonstrates the elution time of standard polysaccharides and FIG. 4b shows the molecular weight profile of Compound G.

Figure 4B:
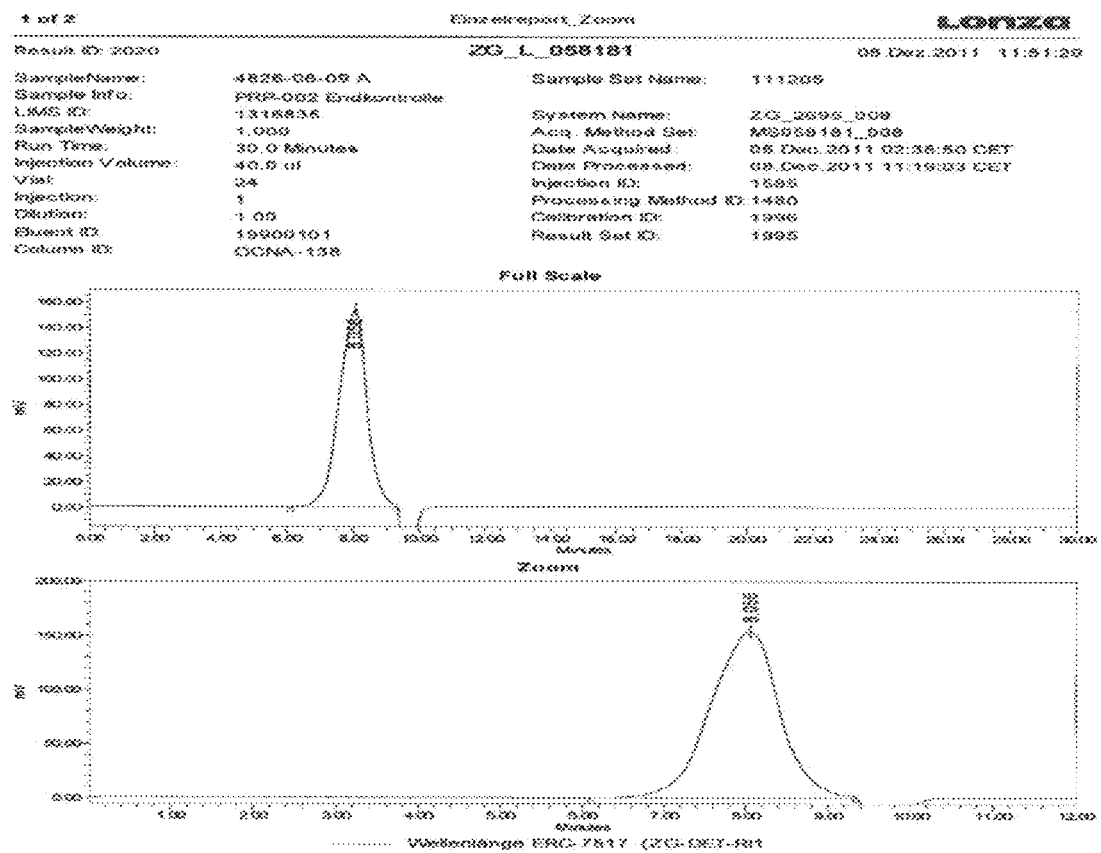
FIG. 4b shows the profile of the selectively depolymerized compound (Compound G) of the instant invention as characterized by Refractive Index (RI) detector.

From this analysis and as shown in FIG. 4b, range of molecular weight of Compound G is from 20 to 70 kDa.

Example 4: Determination of Glycosyl Composition of Compound G

Glycosyl composition analysis was performed by combined gas chromatography followed by mass spectrometry (GC/MS) of the per-O-trimethylsilyl (TMS) derivatives of the monosaccharide methyl glycosides produced from the sample by acidic methanolysis.

An aliquot of each sample was taken and added to tube with 20 ug of inositol as the internal standard. Methyl glycosides were then prepared from the dry sample following methanolysis in 3 M HCl in methanol at 80° C. (6 hours), followed by re-N-acetylation with pyridine and acetic anhydride in methanol (for detection of amino sugars). The sample was then per-O-trimethylsilylated by treatment with Tri-Sil (Pierce) at 80° C. (0.3 hours). These procedures were carried out as previously described in Merkle and Poppe (1994) *Methods Enzymol.* 230: 1-15; York, et al. (1985)

*Methods Enzymol.* 118:3-40. GC/MS analysis of the TMS methyl glycosides was performed on an AT 6890N GC interfaced to a 5975B MSD, using a Supelco EC-1 fused silica capillary column (30 m×0.25 mm ID).

The results of the composition analysis are listed in the table below:

TABLE 2

Mol % of monosaccharide residues of Compound G by GC-MS

| Sample | Glycosyl residue | Mass (g)* | Mol %[1] |
|---|---|---|---|
| Comp G | Arabinose (Ara) | 13.4 | 5.6 |
| Lot # | Rhamnose (Rha) | 9.0 | 3.4 |
| S126K4208 | Fucose (Fuc) | n.d. | — |
| | Xylose (Xyl) | 5.2 | 2.2 |
| | Glucuronic Acid (GlcA) | n.d. | — |
| | Galacturonic acid (GalA) | 220.8 | 71.7 |
| | Mannose (Man) | n.d. | — |
| | Galactose (Gal) | 45.4 | 15.9 |
| | Glucose (Glc) | 3.3 | 1.2 |

HSQC, and gHMBC NMR spectra were acquired on a Varian Inova-500 MHz spectrometer at 343 K (70° C.). Chemical shifts were measured relative to internal acetone (oH=2.225 ppm, oC=31.07 ppm).

Table 3 below indicates approximate ratios of methyl galacturonate to galacturonic acid, and of methyl galacturonate and galacturonic acid to galactose, obtained from 2-D HSQC NMR of Compound G:

TABLE 3

| | Compound G | SD* |
|---|---|---|
| GalA-6-OMe/GalA | 1:2 | |
| GalA(-6-OMe)/Gal | 2:1 | |

The major components in Compound G are 4-linked galacturonic acid, 4-linked methyl galacturonate, and 4-linked galactose. Rhamnose is clearly present in the HSQC spectrum. Table 4 contains the NMR spectral assignment of Compound G.

TABLE 4

| Residue | | Position | | | | | |
|---|---|---|---|---|---|---|---|
| | | 1 | 2 | 3 | 4 | 5 | 6 |
| 4-α-GalAp | $^1$H | 5.08 | 3.77 | 3.98 | 4.42 | 4.69 | |
| | $^{13}$C | 100.0 | 69.5 | 69.9 | 79.3 | 72.3 | 175.9 |
| 4-α-GalApOMe$^a$ | $^1$H | 4.92 | 3.75 | 3.99 | 4.47 | 5.10 | |
| | $^{13}$C | 100.8 | 69.5 | 69.9 | 79.3 | 71.5 | 172.1 |
| 4-β-Galp | $^1$H | 4.62 | 3.69 | 3.77 | 4.16 | 3.72 | 3.81/3.73 |
| | $^{13}$C | 105.5 | 73.1 | 74.2 | 78.5 | 75.4 | 61.7 |
| t-α-Araf | $^1$H | 5.17 | 4.13 | 3.97 | 4.06 | 3.83/3.73 | |
| | $^{13}$C | 107.8 | 82.0 | 77.4 | 84.8 | 62.1 | |
| 5-α-Araf | $^1$H | 5.08 | 4.14 | 4.02 | 4.21 | 3.88/3.80 | |
| | $^{13}$C | 108.6 | 82.0 | 77.7 | 83.2 | 67.6 | |
| Rhap | $^1$H | n.d. | n.d. | 3.89 | 3.40 | 3.79 | 1.25 |
| | $^{13}$C | n.d. | n.d. | n.d. | n.d. | n.d. | 17.6 |

$^a$methyl resonance: 3.81/53.9 ppm

TABLE 2-continued

Mol % of monosaccharide residues of Compound G by GC-MS

| Sample | Glycosyl residue | Mass (g)* | Mol %[1] |
|---|---|---|---|
| | N-AcetylGalactosamine (GalNAc) | n.d. | — |
| | N-AcetylGlucosamine (GlcNAc) | n.d. | — |
| | N-AcetylMannosamine (ManNAc) | n.d. | — |
| | Total | 297.1 | CHO = 99% |

*Assay standard deviation has not been determined

Example 5: Determination of Glycosidic Linkages and Structure by H1 and C13 NMR NMR spectroscopy reveals individual molecular signatures and linkages, providing a type of analytical fingerprint for complex carbohydrate molecules. Two dimensional NMR spectra were evaluated to reveal the molecular fingerprint of the composition of the instant invention, Compound G, and comparison to Compound S.

Figure 5A:
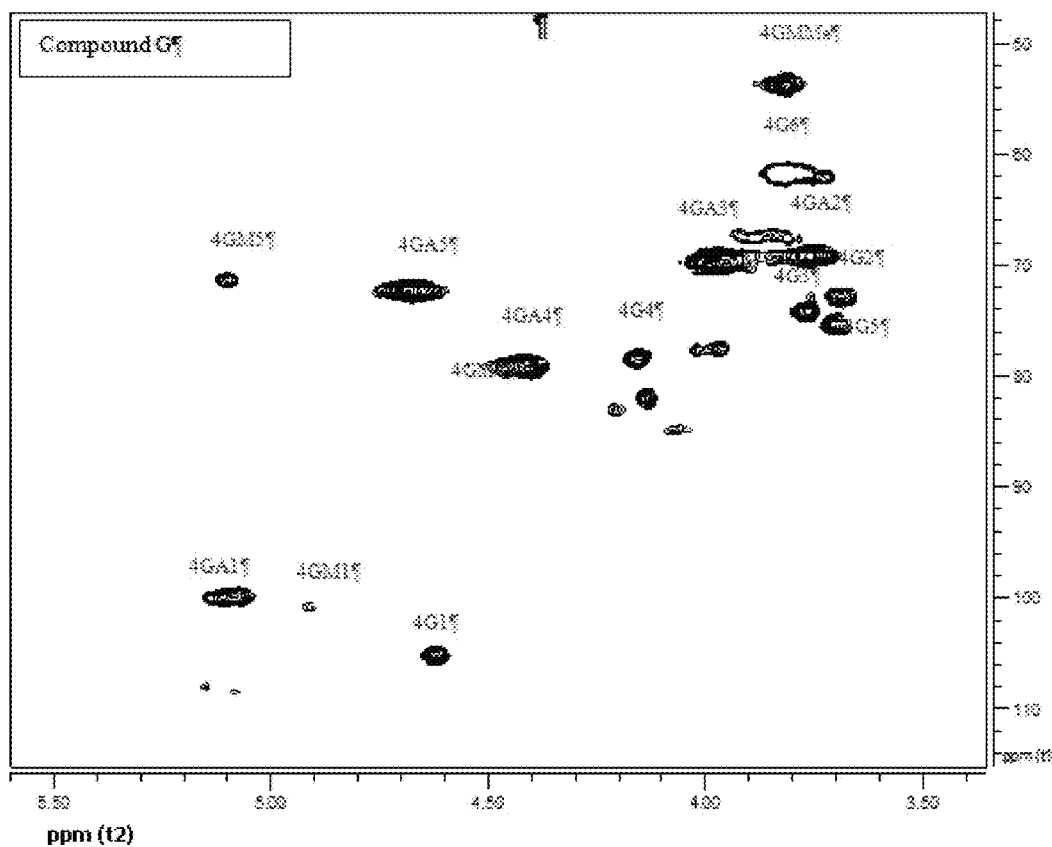
FIG. 5a shows two dimensional NMR (2-D NMR) of the combined spectrum of D1 and C13 NMR for Compound G. This two dimensional NMR depicts a finger-printing identification of the glycosidic linkages of Compound G.
Figure 5B:
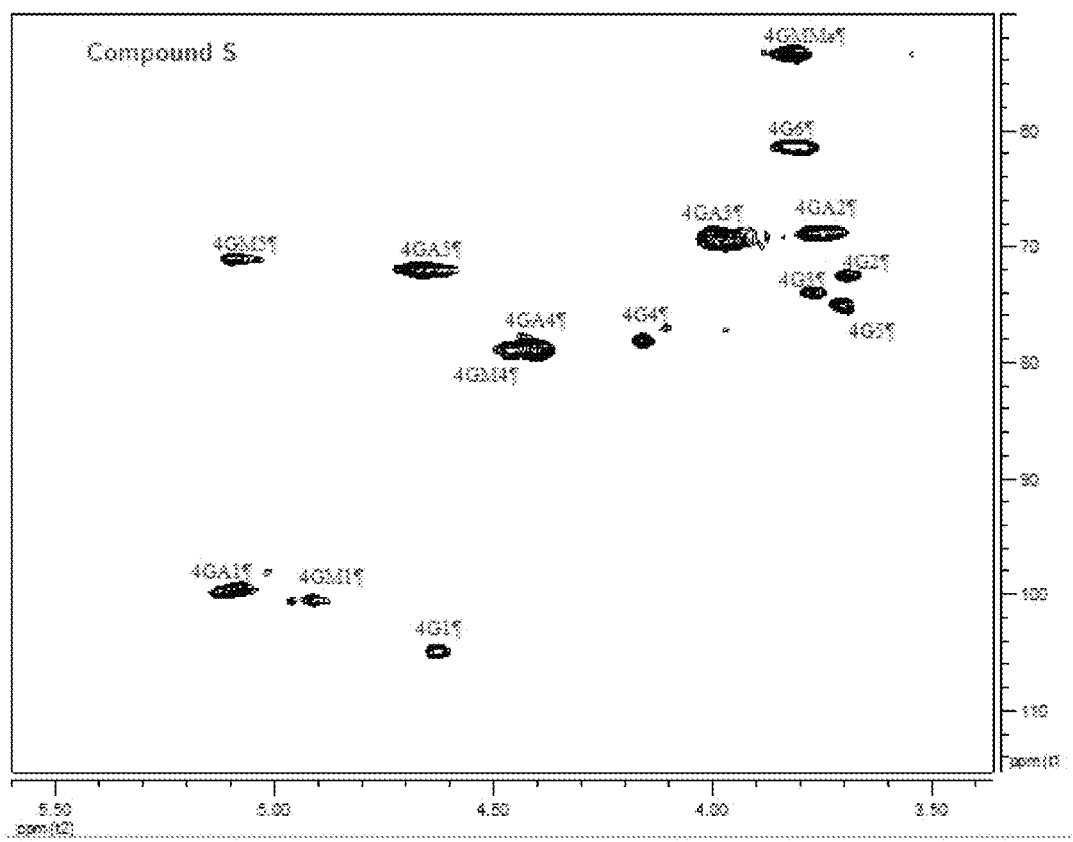
FIG. 5b shows two dimensional NMR (2-D NMR) of the combined spectrum of D1 and C13 NMR for Compound S.

For NMR spectroscopy, the samples of Compound G and Compound S were dissolved in 0.7 mL D20 (99.96% D), and transferred to a 5-mm NMR tube (Wilmad). 1-D Proton and 2-D TOCSY, NOESY, gradient enhanced COSY (gCOSY), FIG. 5a shows the two dimensional NMR spectrum for Compound G and FIG. 5b shows the two dimensional NMR spectrum for Compound S.

Comparison of two dimensional NMR spectra from different samples of modified pectin material is a powerful method for evaluating different structures.

Figure 5C:
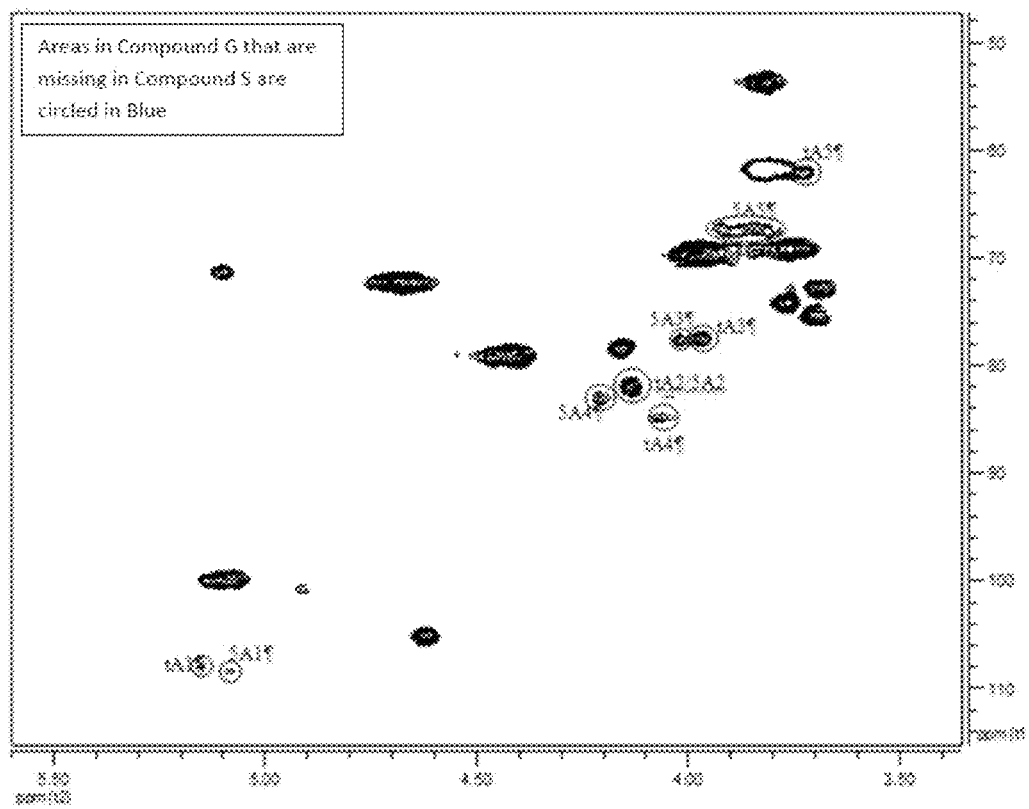
FIG. 5c shows an overlap comparison of these spectra demonstrating the differences between Compound G and Compound S. The circled signals are specific to Compound G.

FIG. 5c shows the overlapping spectra of Compound G and Compound S, revealing the marked differences in the two dimensional NMR spectra of these two compounds. The positions that are circled are in the spectrum of Compound G, but not in Compound S. This indicates important structural differences between Compound G and Compound S.

This analysis demonstrates clear structural differences between Compound G and Compound S, made by a different manufacturing method. These structural differences are evident on two dimensional NMR analyses when the chemical composition analysis, which measures only the monosaccharide composition, does not show gross differences.

Two dimensional NMR fingerprinting can be included in the certificate of analysis for GMP batches of Compound G as a precise evaluation of the complex molecular structure.

Example 6: Determination of Compound G Cytotoxicity to Cultured Cell Lines

One of the prominent features of modified pectin compounds that have been reported (U.S. Pat. No. 8,128,966 and U.S. 2012/0149658) is their cytotoxicity in cell lines of various types, including the induction of apoptosis. For example U.S. Pat. No. 8,128,966 discloses modified pectins that induce apoptosis in cancer cells, such as B16-F10 melanoma cell line.

Unlike the results of U.S. Pat. No. 8,128,966, the modified pectin of the present invention, was shown to have no cytotoxicity when used in a variety of cell lines, including B16-F10 melanoma cells.

Human hepatic stellate cell line, LX-2 is routinely used as a tool for analysis of hepatic fibrosis. The LX-2 cells proliferate normally in 2% FC serum rich media. However, once stress in 0.1% FC serum, LX-2 cells go through similar pathological changes as established in fibrotic liver. Cytotoxicity was assessed using Compound D, Compound H, and Compound G.

Figure 6A:
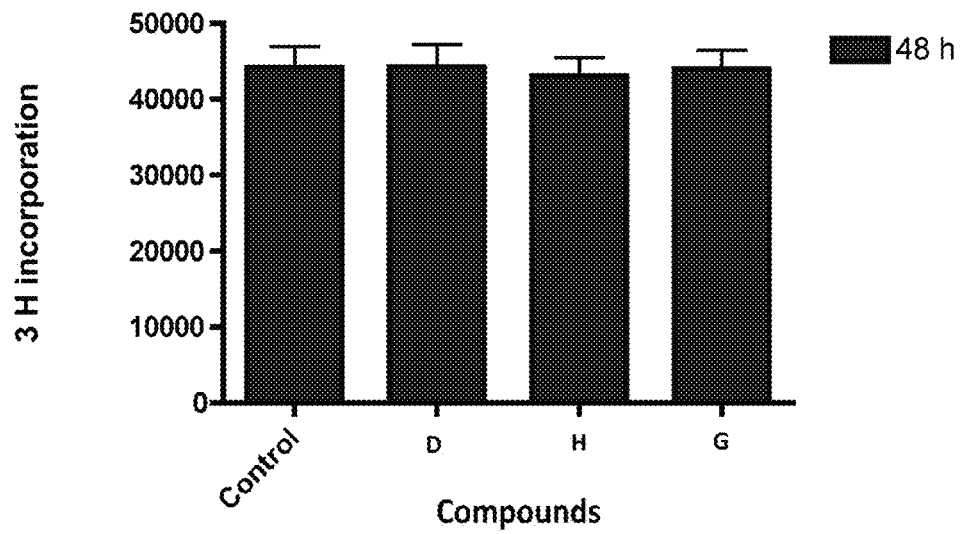
FIG. 6a-d is a depiction of various types of experiments demonstrating the lack of cytotoxicity and apoptosis of Compound G on cultured stellate liver cell line LX-2.

FIG. 6a shows the results of a proliferation assay utilizing the incorporation of tritium-labeled thymidine into growing LX-2 cells. There was no difference from control cells in thymidine incorporation at 48 hours of culture when cells were incubated with 1 mg/ml of Compound D, Compound H, or Compound G.

Figure 6B:
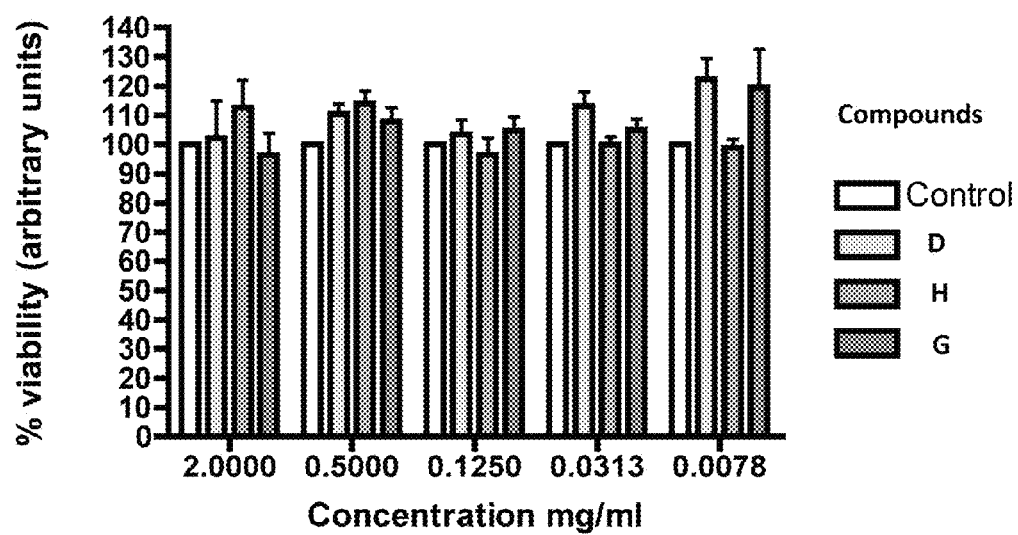

FIG. 6b shows the results of a cell viability assay utilizing a vital dye which is taken up by non viable cells and excluded from viable cells. There was no difference from control cells in cell viability at 48 hours of culture when cells were incubated with 1 mg/ml of Compound D, Compound H, or Compound G.

The presence of apoptosis was also evaluated using the annexin apoptosis kit (eBioscience). Annexins are a family of calcium-dependent phospholipid binding proteins that preferentially bind phosphatidylserine (PS). Under normal physiologic conditions, PS is predominantly located in the inner leaflet of the plasma membrane. Upon initiation of apoptosis, PS loses is asymmetric distribution across the phospholipid bilayer and is translocated to the extracellular membrane leaflet marking cells as targets of phagocytosis. Once on the outer surface of the membrane, PS can be detected fluorescently labeled Annexin V in a calcium-dependent manner.

Figure 6C:
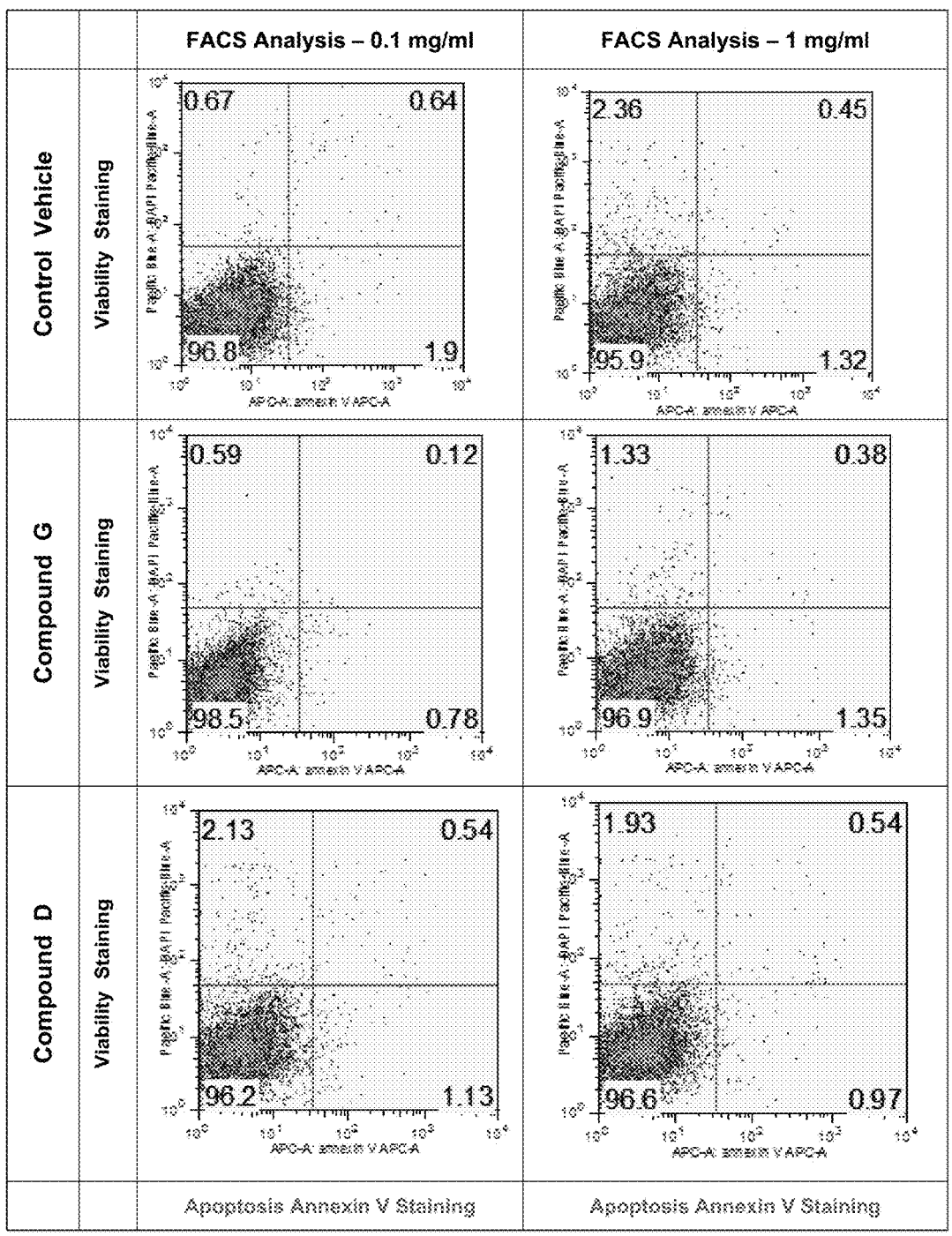

FIG. 6c shows the results of FACS (Fluorescence activated cell sorting) analysis of LX-2 cells to assess apoptosis which showed no evidence of apoptosis in cells treated with Compound D or Compound G versus control cells (vehicle treated).

Figure 6D:
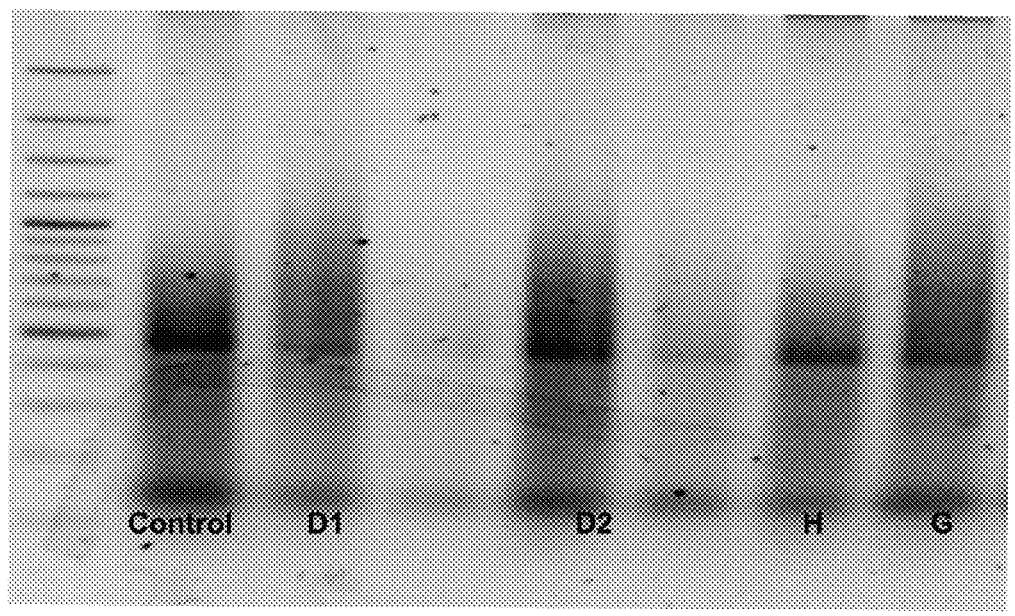

As a further test for apoptosis, LX-2 cells were examined for the presence of DNA fragmentation. FIG. 6d shows that there was no evidence of DNA fragmentation in cells treated with Compound D (D1 or D2), Compound H or Compound G as compared to control.

Figure 7:
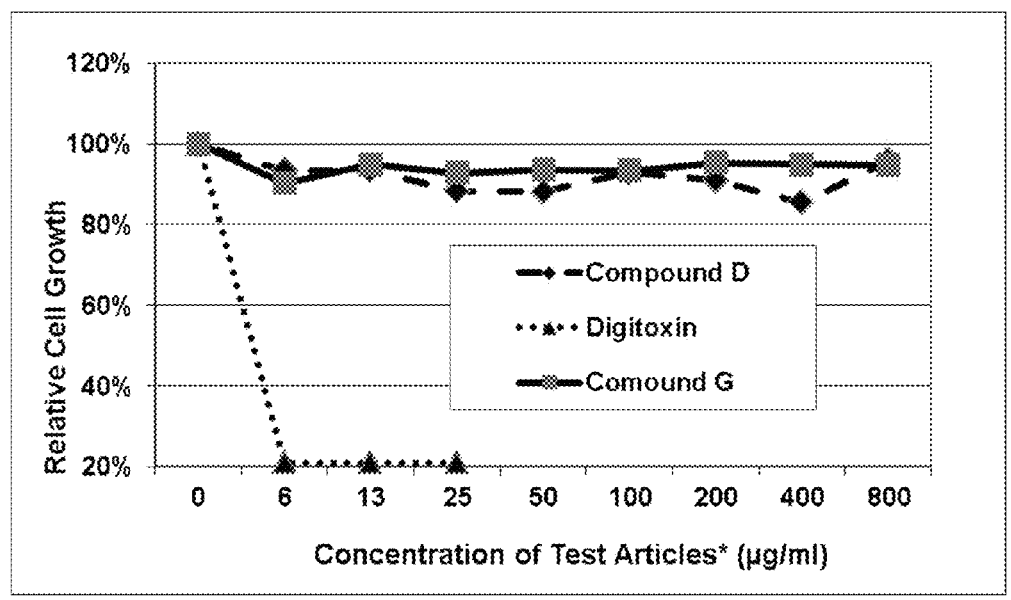
FIG. 7 is a graph showing the relative cytotoxicity on the monocyte/macrophage cell line THP-1 following 3 days in the presence of Compound G of the present invention (square), Compound D, a galactomannan product (diamond) and digitoxin (triangle).

Macrophages are integrally involved in inflammatory and fibrotic processes. Thus, a macrophage cell line THP-1 (ATCC® Number: TIB-202™) was evaluated for the effect of Compound G on cytotoxicity as shown in FIG. 7. The THP-1 cell line is a monocyte type cells line harvested from peripheral blood of patient (Homo sapiens) with Acute Monocytic Leukemia (AML) (see Tsuchiya S, et al. Induction of maturation in cultured human monocytic leukemia cells by a phorbol diester. Cancer Res. 42: 1530-1536, 1982).

The THP-1 cells were suspended in assay media containing 10% FBS. About 25,300 cells/well were transferred at 100 ul/well to 96 well plates. At 24 hours the culture media was changed to fresh media and the cells were incubated over night. Test compounds were serially diluted in assay media containing 10% FBS and transfer 100 ul/well to the growing monocyte cells THP-1. The final assay volume was 200 ul/well containing 10% FBS, 2× Gentamicin, and the following test articles: Compound G of the present invention and Compound D, a galactomannan product or in presence of digitoxin. The cells were incubated for 3 days with the test articles. After removing 50 ul of supernatant for other testing, cytotoxicity/growth was measured by adding 15 ul of Promega "CellTiter 96® Aqueous One Solution" to the 96 wells and viability was monitored at OD 490 nm after 1-7.5 hours. The CellTiter 96® AQueous One Solution Cell Proliferation Assay is a colorimetric method for determining the number of viable cells in proliferation, cytotoxicity or chemosensitivity assays. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution for detection cell viability in in-vitro culture media.

FIG. 7 shows that increasing amounts of Compound G applied to THP-1 cells did not result in cytotoxicity.

The melanoma cell line B16-F10 was previously used as an assay for activity of modified pectins. Thus, B16-F10 cells were evaluated for the effect of Compound G on cytotoxicity.

The melanoma cell line B16-F10 (ATCC® Number: CRL-6475™) are a mixture of spindle-shaped and epithelial-like cells from skin melanoma of mouse (Mus musculus, Strain: C57BL/6J (See Fidler I J. Biological behavior of malignant melanoma cells correlated to their survival in vivo. Cancer Res. 35: 218-224, 1975.)

Melanoma cells B16-F10 were transferred to a fresh media (DMEM—10% Fetal Bovine Serum—FBS). About 2,900 cells/well (passage #4) were transferred in 100 ul/well to 96 well plates for overnight incubation. At 24 hours the culture media was changed to fresh serum free media and incubated over night. Test compounds were serially diluted in assay media containing 1% FBS and 100 ul/well was transferred to the growing melanoma cells. The final assay volume was 200 ul/well containing 1% FBS, 2× Gentamicin, and compound G of the present invention, compound D, a galactomannan product or 5-fluorouracil. The cells were incubated for 3 days with the test compounds. Cytotoxicity/growth was measured by adding 20 ul of Promega "CellTiter 96® Aqueous One Solution" to the 96 wells and monitored at OD 490 nm after 1 hour. The CellTiter 96® AQueous One Solution Cell Proliferation Assay is a colorimetric method for determining the number of viable cells in proliferation, cytotoxicity or chemosensitivity assays. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution for detection cell viability in in-vitro culture media.

Figure 8:
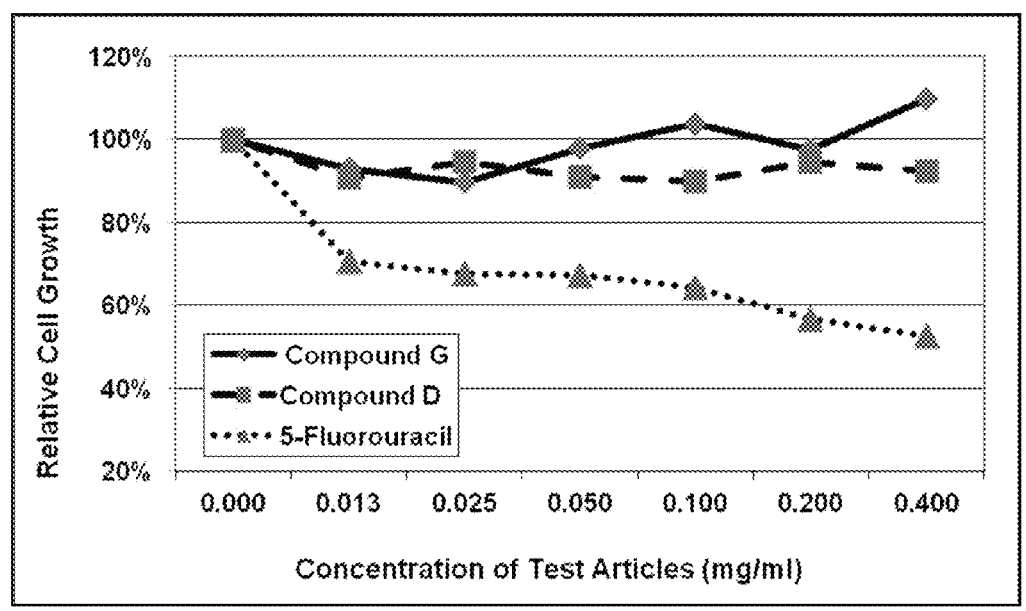
FIG. 8 is a graph showing the relative cytotoxicity on cultured melanoma cell line B16-F10 following 3 days in the presence of Compound G of the present invention (diamond), Compound D, a galactomannan product (square) and 5-Fluoruracil (triangle).

FIG. 8 shows that increasing amounts of Compound G applied to B16-F10 cells did not result in cytotoxicity. This represents a clear difference from the function of other modified pectin compounds previously described.

PBMC cells are primary cell extracted from whole blood using ficoll, a hydrophilic polysaccharide. Peripheral blood mononuclear cells (PBMC) are integrally involved in inflammatory and fibrotic processes. Thus, PBMC were evaluated for the effect of Compound G on cytotoxicity.

Figure 9:
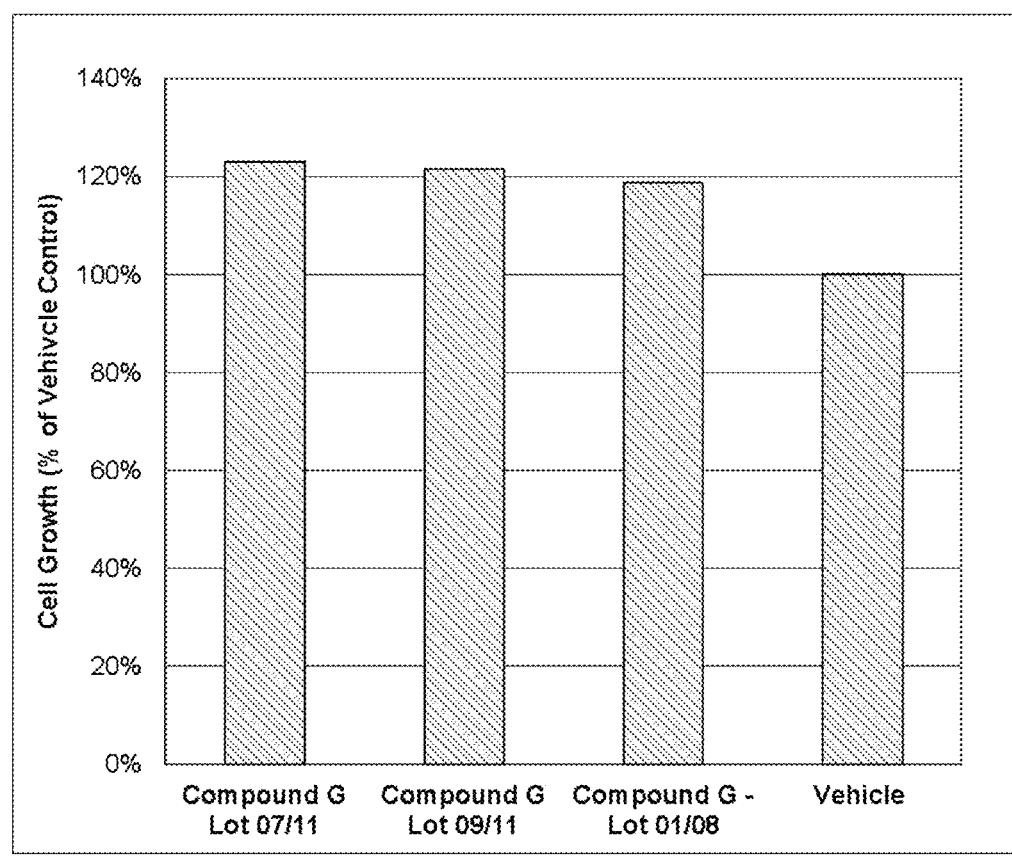
FIG. 9 is a graph showing the lack of cytotoxicity of Compound G on cultured peripheral blood mononuclear cells (PBMC), a primary cell culture.

FIG. 9 shows that Compound G from three different lots applied to PBMCs did not result in cytotoxicity. Compound G at concentrations of up to 500 ug/mL had no effect on the growth of PBMC. Cytotoxicity was measured using MTS assay (CellTiter 96® AQueous One Solution Cell Proliferation Assay (MTS) Promega USA.)

Figure 10:
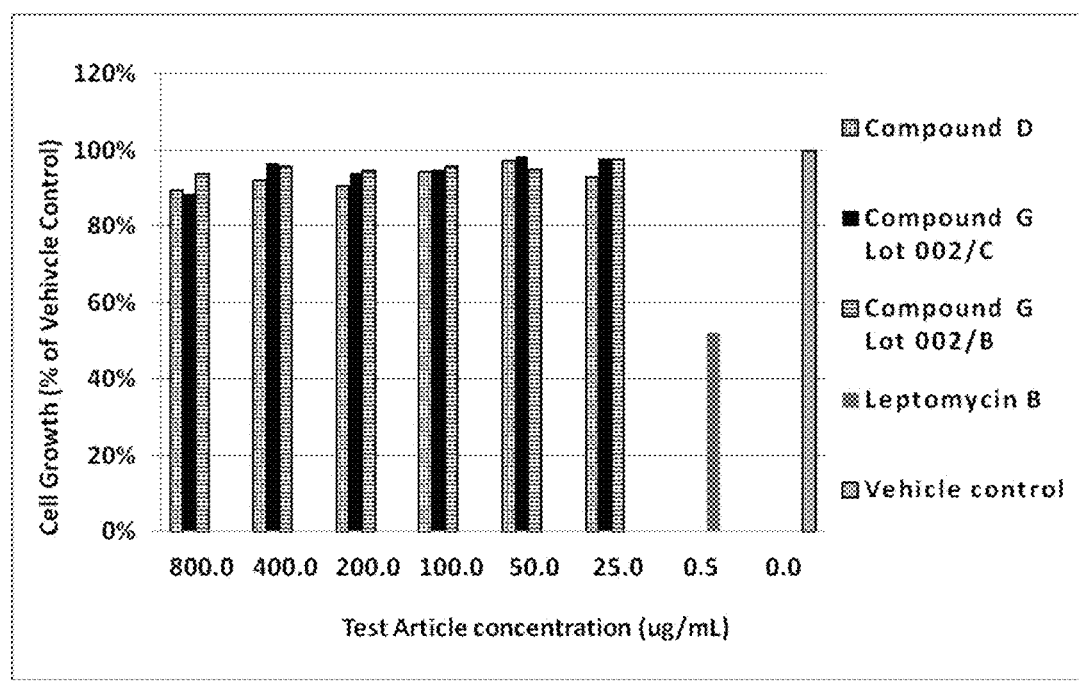
FIG. 10 is a graph showing the lack of cytotoxicity on growth of lung fibroblast (MRC-5*) cells after 4 days growth in present of Compounds G and Compound D. Cytotoxicity was measured using MTS assay.

FIG. 10 shows that increasing amounts of Compound G applied to cultured lung fibroblast cells did not result in cytotoxicity. The MRC-5 cell line is a normal fibroblast that was derived from normal lung tissue (Homo sapiens (human) male (ATCC Catalog No. CCL-171™). Increasing amounts of the following test articles: Compound G of the present invention, Compound D, a galactomannan product were tested using a CellTiter 96® AQueous One Solution Cell Proliferation Assay (MTS)-Promega USA. FIG. 10 shows that Compound G at up to 800 ug/mL had no effect on the growth of lung fibroblast in vitro.

The summary of these data show convincingly that Compound G is not cytotoxic to cells and does not induce apoptosis. This is in contrast to all the other reports of modified pectin materials reported.

Example 7: In-Vitro Assay for Anti-Inflammatory Effect Using PBMC Primary Cells

Compound G was assessed for its biological activity in inflammatory conditions. Multiple cells are involved in and activated in the inflammatory process. One key cell type in this process are Peripheral Blood Mononuclear Cells (PMBCs), a primary cell routinely use as anti-inflammatory in-vitro model, which are activated by inflammatory mediators, recruited to sites of inflammation, transform into tissue macrophages, and enhance the inflammatory process. Therefore, PBMCs were used as an in vitro model to evaluate the effect of Compound G.

The in-vitro assay for inflammation was developed by stressing PBMC with microbial endotoxin (microbial lipopolysaccharides) and measuring by secretion of TNF alpha, a major cytokine and biomarker for inflammation. PBMC were re-suspended in assay media containing 10% FBS (Gibco lot #749413), 2× Gentamicin, and L-Glutamine. PMBC were transferred 90 µl/well to assay plate (169,000 cells/well). 90 µl/well of assay media was added to assay plate to a total volume of 180 µl/well for approx. 16 hours. LPS (microbial toxin) was serially diluted in assay media. 20 µl/well of LPS were added to assay plate to a final volume of 200 µl/well and incubated for 7 hours at 37 degrees C. 60 µl/well were removed for TNF-α (Transforming Nuclear Factor alpha) ELISA assay. The 60 µl samples were diluted 1:4 with ELISA diluent (total volume is 240 µl) and 100 µl/well sample were transferred to an ELISA plate. h-TNF-α was analyzed using an ELISA Development Kit (PeproTech, cat #900-K25, lot #0509025), with Human TNF-α as standard on an ELISA plate. 100 µl of ABTS Liquid Substrate was added to each well and OD was read at 405 nm with a wavelength correction set at 650 nm.

The plate plan used is set out below:

| Plate Plan: | 1 | 2 | 3 | 4 | 5 | 6 | 7 | 8 | 9 | 10 | 11 | 12 |
|---|---|---|---|---|---|---|---|---|---|---|---|---|
| A | h-TNFa STD; 5 ng/ml (1:2) | | LPS; 400 ng/ml (1:2) | | | | | | | | h-INFa STD; 5 ng/ml (1:2) | |
| B | | | | | | | | | | | | |
| C | | Compound S; 1.0 mg/ml (1:2); Assay | | | | | | | | | | |
| D | | Media Containing 50 ng/ml LPS | | | | | | | | | | |
| E | | Compound D; 1.0 mg/ml (1:2); Assay | | | | | | | | | | |
| F | | Media Containing 50 ng/ml LPS | | | | | | | | | | |
| G | | Compound G; 1.0 mg/ml (1:2); Assay | | | | | | | | | | |
| H | | Media Containing 50 ng/ml LPS | | | | | | | | | | |

Figure 11:
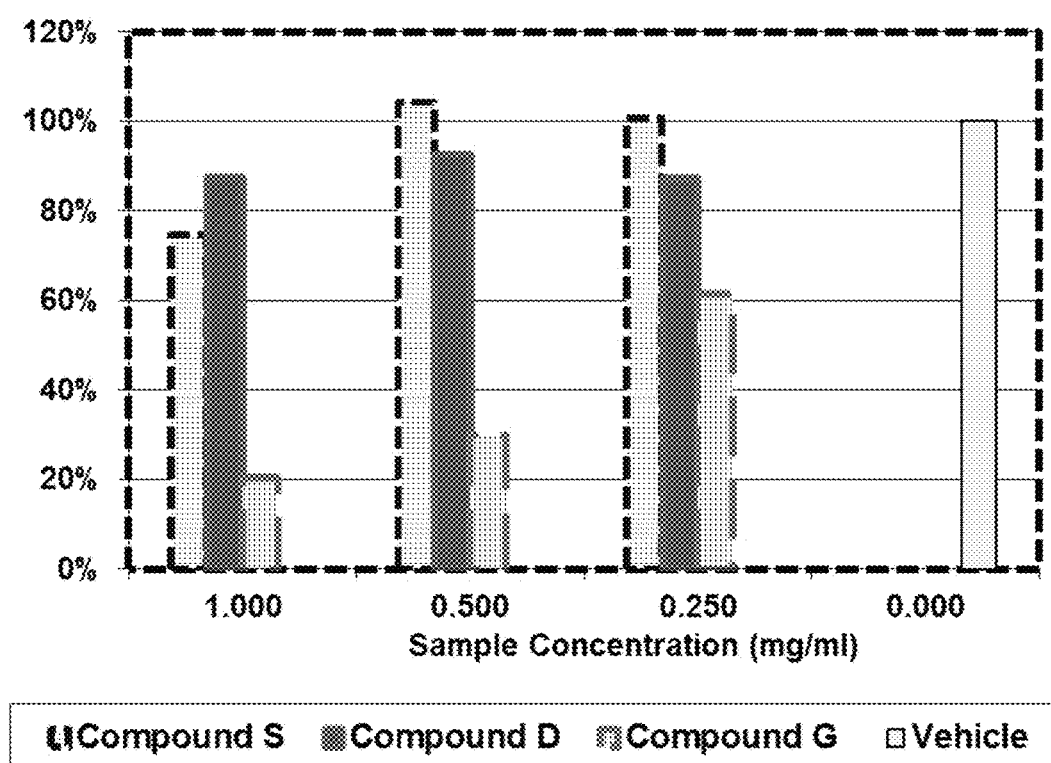
FIG. 11 is a graph showing the relative anti-inflammatory effect of three modified polysaccharides including compound G of the current invention, on secretion of TNF-alpha by PBMC cells stressed with microbial endotoxin (50 ng/ml).

FIG. 11 demonstrates graphically results of Plate 364 with h-TNF alfa ELISA. Compound G at 0.5 mg/mL reduced 50% of TNF-alpha secretion by stressed PBMC primary cells. The reduction of TNF-alpha secretion is significantly higher than either Compound D or Compound S reference polysaccharides tested.

Figure 12:
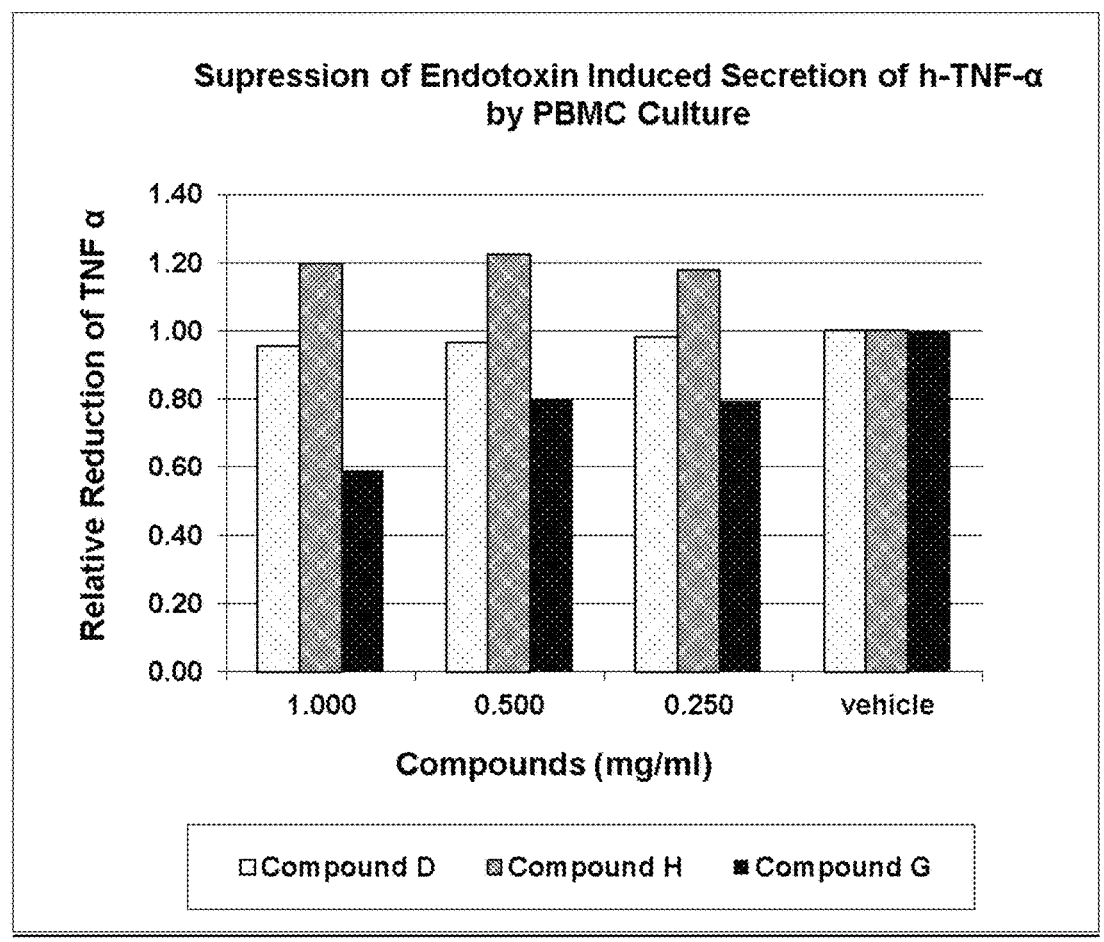
FIG. 12 is a comparison of Compound G of the present invention and Compound H on the secretion of TNF-alpha by PBMC cells stressed with microbial endotoxin (50 ng/ml).

The ability of Compound D, Compound H, and Compound G to inhibit TNF-alpha secretion in PBMC were directly compared, as shown in FIG. 12. Compound H was produced using the method disclosed in U.S. Pat. No. 8,236,780. Compound D and Compound H did not show any ability to reduce TNF-alpha secretion from PBMC cells, in fact Compound H appeared increase TNF-alpha. In contrast, Compound G significantly inhibited secretion of TNF-alpha.

Compound G was shown to be a potent inhibitor of an in vitro model of inflammation. Such activity was shown to be absent from Compound S or Compound H, modified pectin compounds made through different processes from Compound G. Therefore, results form Examples 6 and 7 showed that Compound G is modified pectin having unique non-cytotoxic and anti-inflammatory properties that were not described for other known pectin-derived compounds.

Example 8: In-Vitro Induction of Fibrogenesis in Liver LX-2 Stellate Cell Line

In other experiments, the inventors have shown that human cultured stellate cell lines (LX-2) express and secrete into the medium galectin-1 and galectin-3 upon stressing the cells by reducing the FC serum in the culturing media from 2% to 0.1%.

Human hepatic stellate cell line, LX-2 is routinely used as a tool for analysis of hepatic fibrosis. The LX-2 cells proliferate normally in 2% FC serum rich media. However, once stress in 0.1% FC serum they go through a similar pathological changes as established in fibrotic liver The Compound G may also modulate, increase or decrease in LX-2 stellate cells molecules or biomarkers that are involved in fibrogenesis, including but not limited to collagen I, II, III, IV, metalloproteases, inhibitors of metalloproteases, and cytokines.

The Compound G compound may also modulate expression of cytokines and lipids and reactive oxygen species in liver macrophages, or Kupffer cells.

The Compound G compound may also modulate the expression of hepatocellular genes, uptake and metabolism of lipids and reactive oxygen species.

The effect of Compound G on the expression of galectin-3 in both intra and extra-cellular compartments was assessed, as shown in FIG. 13. While rich serum media had produced negligible amount of galectin-3, when LX-2 cells (human stellate cell line) were stressed with growth media depleted of fetal calf serum (in only 0.1% serum media), a model which have been shown to be an in-vitro model for fibrogenesis, galectin-3 was expressed reaching maximum at about 5 to 7 days post culture in 0.1% serum media. An immunochemistry staining technique demonstrated increased expression of galectin-3 at day 6 post-stress in 0.1% serum, while the addition of compound G was shown to significantly suppress the expression of galectin-3.

Example 11: Assessment of Therapy in a TAA-Induced Liver Fibrosis Model

In order to determine if the compound of the instant invention has an anti-fibrotic biological activity in living animals, a preliminary feasibility test was conducted in vivo. Severe liver fibrosis was induced by chemical toxicity of biweekly administration of thioacetamide (TAA). Compound G was given IP at 90 mg/kg weekly for 4 weeks, and compound D was given at dose of 180 mg/kg weekly for 4 weeks. The experimental design is shown in FIG. 14.

Figure 15:
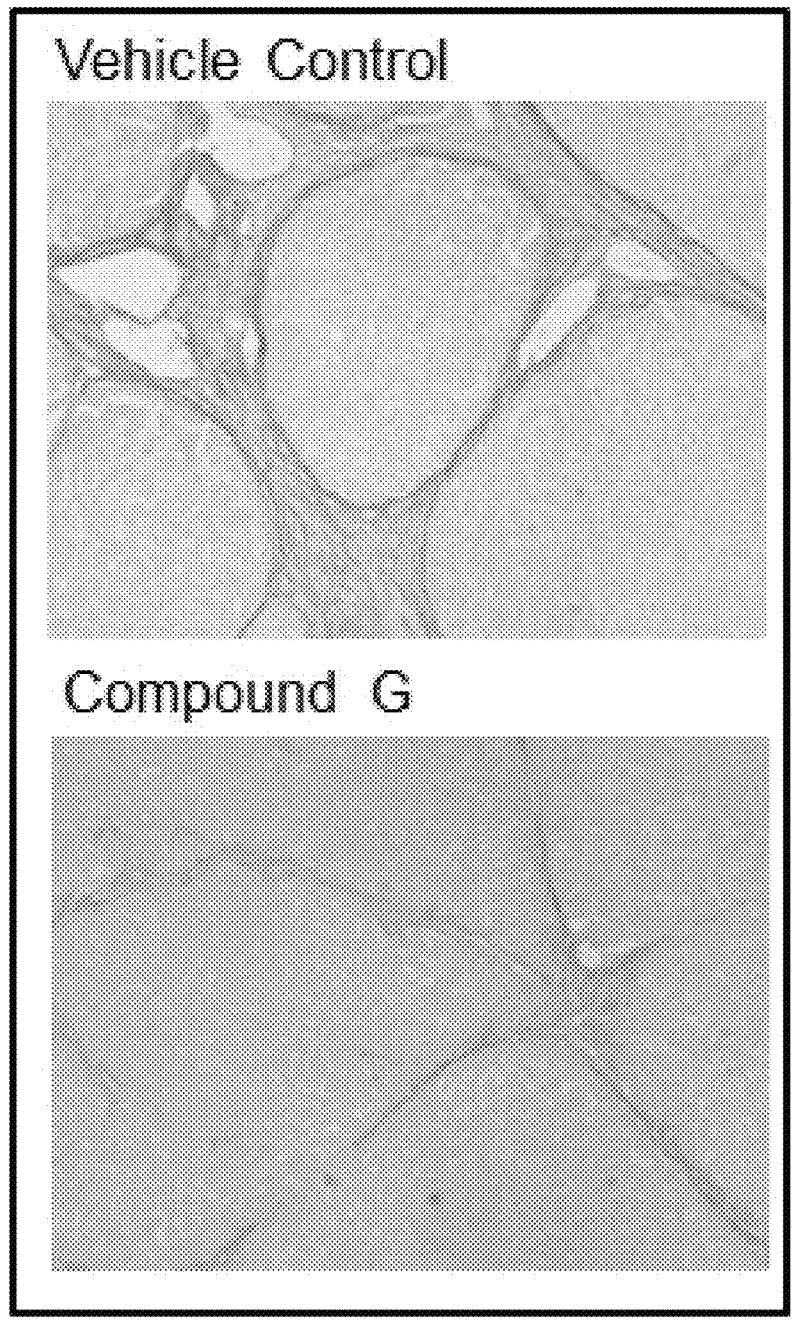
FIG. 15 is a photographic depiction of histological regression of fibrosis (Sirius Red staining for collagen) after 4 weekly treatments with Compound G of TAA-induced liver fibrosis.

After 8 weeks of treatment with TAA, Sirius red staining of the fibrotic liver (vehicle control) showed extensive infiltration of fibrotic tissue (FIG. 15). In contrast, the fibrotic material was markedly reduced, and nearly eliminated in some areas in the liver from an animal treated with Compound G (FIG. 15).

Statistical analysis of fibrosis grade and percent collagen was performed with animals treated with Compound G and Compound D (FIG. 16).

FIG. 16 shows a statistically significant reduction in fibrotic area measured by digital morphometric analysis of Sirius red-stained liver sections when animals were treated with Compound G and Compound D when compared to vehicle controls, with greater reduction seen with Compound G when compared to Compound D.

These experiments demonstrate anti-fibrotic activity of Compound G, which correlates with its anti-inflammatory effect demonstrated in cell lines.

Example 12: Assessment of Therapy in Mouse Fatty-Liver NASH Model

Figure 17:
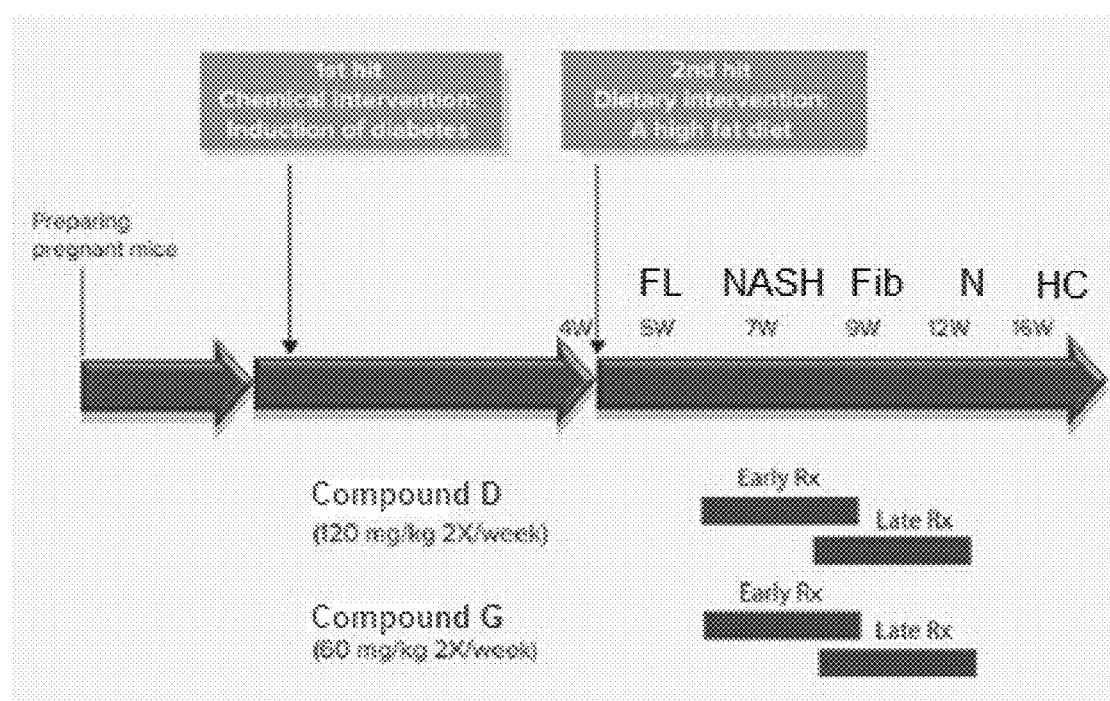
FIG. 17 is a depiction of the mouse fatty-liver fibrosis model, a NASH experimental model associated with metabolic disorder (severe diabetes) and high fat diet. Also shown is the experimental design of treatment with Compound G and Compound D.

The effect of galectin binding carbohydrates in the therapy of experimental fatty liver disease and NASH was examined. STAM mice in which diabetes was induced and a high fat diet was administered were used as an experimental model. This is a proven model in which the mice consistently develop NASH with hepatocyte fat accumulation, evidence of hepatocyte toxicity, portal and lobular inflammatory infiltrates, peri-sinusoidal fibrosis, advanced fibrosis with nodule formation, cirrhosis, and ultimately hepatocellular carcinoma in a certain percentage of animals. NASH mice were treated biweekly IV at 9-12 weeks of study, as shown in FIG. 17.

STAM mice were used to explore the effect of Compound G. In the study two compounds have been tested, Compound D (as described in U.S. Pat. No. 7,893,252) and Compound G on the histopathological findings associated with NASH in the liver (FIG. 17). In the STAM model, neonatal mice were given an injection of streptozotocin which results in endocrine pancreatic insufficiency and diabetes mellitus. At four weeks of age, a high fat diet was introduced which was continued throughout the experiment. This model results in a reproducible disease that includes fatty liver (FL), NASH, NASH with fibrosis (Fib), nodule formation (N) and in a certain percentage of animals hepatocellular carcinoma (HC). In this experimental design, drug therapy was initiated at 8 weeks and continued for a total of 4 weeks. Compound D was administered at a dose of 120 mg/kg dissolved in normal saline intravenously twice a week. Compound G was administered in a dose of 60 mg/kg dissolved in normal saline intravenously twice a week.

Figure 18:
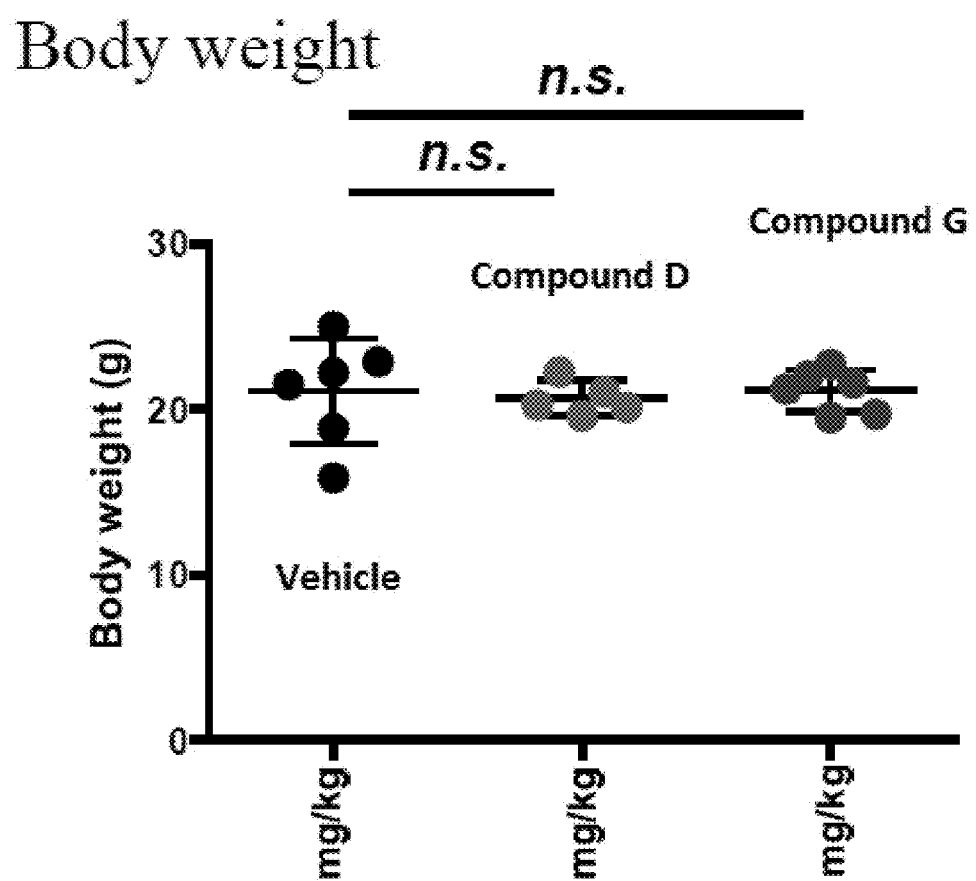
FIG. 18 is a graph showing the change in body weight of NASH mice treated with vehicle, Compound D, or Compound G.

FIG. 18 shows that mice in all groups gained weight over the time of the experiment with no differences between groups. This result indicates at a gross level that there was little toxic effect of the treatments on the animals and any changes detected are unlikely due to the overall health of the animals. Overall there were 2 deaths in the vehicle group (2/12, 17%) and one in the Compound D treated group (1/12, 8%), all related to liver disease as determined by postmortem examination by the veterinarian. There were no deaths in the Compound G treated group. This in vivo activity of lack of toxicity in the mice correlates with the lack of cytotoxicity seen in vitro cell line experiments.

The NAFLD activity score was used to evaluate disease severity and gives points for three aspects of NASH pathology including, steatosis (0 (<5%), 1 (5-33%), 2 (33-66%), or 3 (>66%)), hepatocyte ballooning (0 (none), 1, (few), or 3 (many)), and lobular inflammation (0 (no foci), 1 (<2 foci/200× field), 2 (2-4 foci/200× field), or 3 (>4 foci/200× field)). The total number of points is the NAFLD activity score.

Figures 19A, 19B:
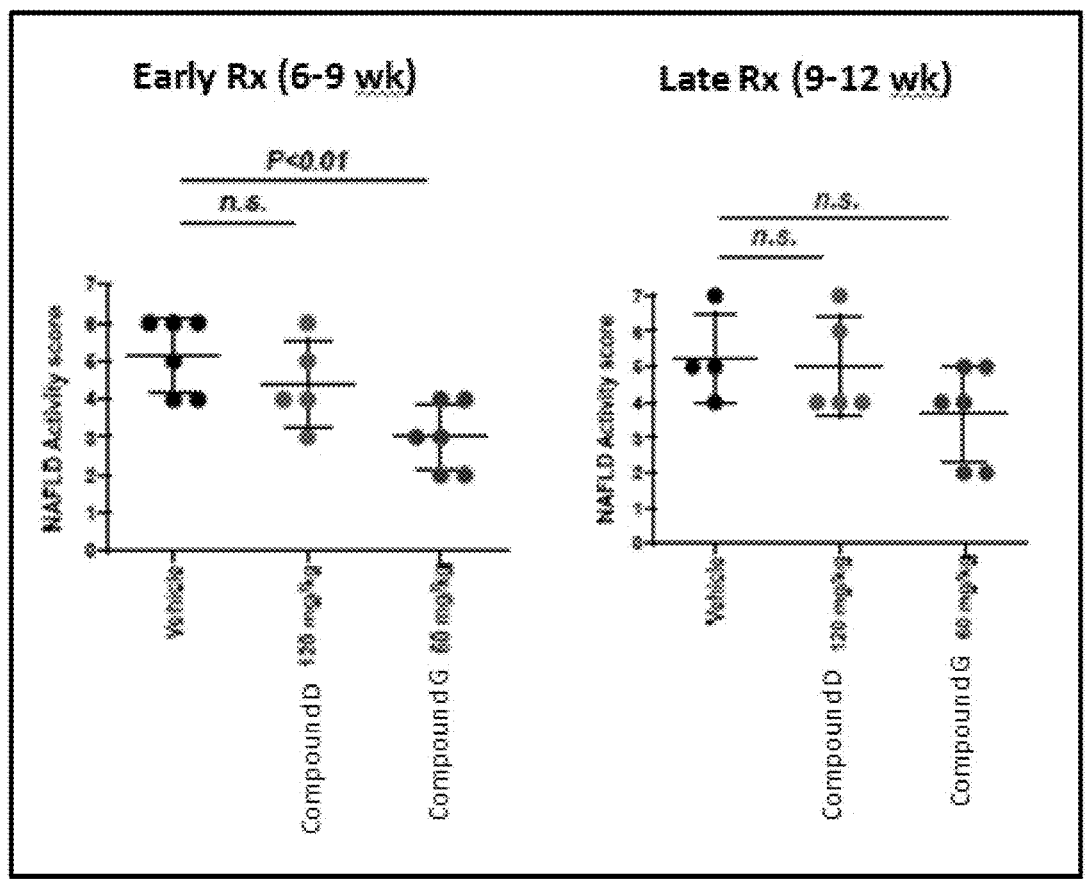
FIGS. 19A-B show the statistical significance of the extent of depicting the extent of liver cell steatosis, ballooning degeneration, and lobular inflammation (as summarized in a NAFLD activity score) in mice treated with vehicle, Compound D, and Compound G.

FIG. 19A and FIG. 19B show a graphical depiction with statistical values of the NAFLD activity score in the three experimental groups. There was an improvement in NAFLD activity score in animals treated with Compound G and less of an effect with Compound D.

Figures 20A, 20B:
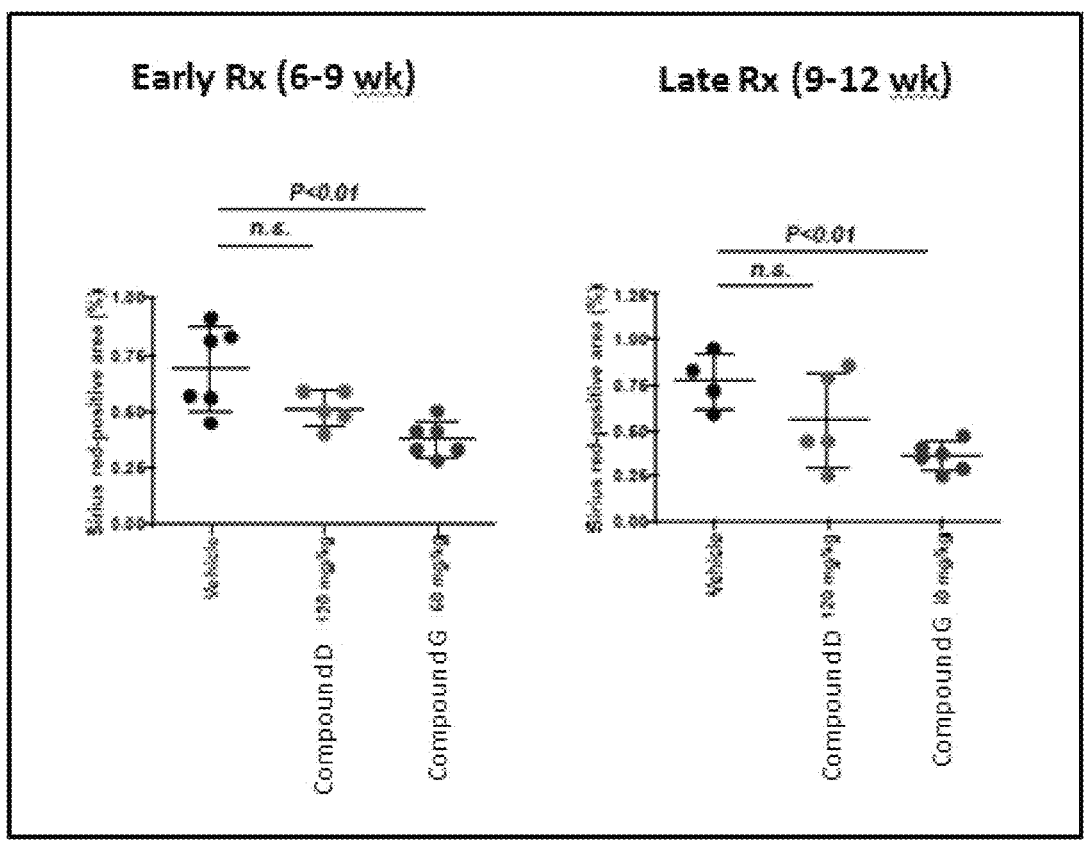
FIGS. 20A-B show the statistical significance of the extent of percent collagen in liver sections as measured by the Sirius Red staining method, for NASH mice treated with vehicle, Compound D, and Compound G.

FIG. 20A and FIG. 20B show a graphical depiction with statistical values of the percent collagen in the three experimental groups. Sirius red is a histological stain that has a specific affinity for collagen fibers, staining them red, and is therefore a quantitative tool for assessing the degree of fibrosis in liver biopsies. The area of Sirius red staining on liver histopathological sections from each of the three treatment groups was assessed using computer assisted morphometric analysis. Animals in both the early and late treatment groups had a marked reduction in collagen proportional area when treated with Compound G. Treatment with Compound D had an intermediate effect on collagen proportional area between vehicle control and Compound G. These results demonstrated that treatment with Compound G significantly reduces liver fibrosis in mice with NASH.

The results in the NASH mice (FIGS. 17-20) extend and confirm the results found in the TAA treated rats on liver fibrosis. Additionally, these experiments show a marked anti-inflammatory effect of Compound G with a reduction in the NAFLD activity score (steatosis, hepatocyte ballooning, and inflammatory infiltrate). The combination of these anti-inflammatory and anti-fibrotic effects in an animal model of NASH correlates with the anti-inflammatory effect demonstrated in the PBMC cell culture model.

It is understood that the examples and embodiments described herein are for illustrative purposes only and that various modifications of changes in light thereof are to be included within the spirit and purview of this application and scope of the appended claims. All publications, patents and patent applications cited herein are hereby incorporated by reference in their entirety for all purposes.

What is claimed is:

1. A composition comprising:
   a. a therapeutically effective amount of an arabinogalactorhamnogalacturonan compound comprising a complex carbohydrate backbone of a 1,4-linked galacturonic acid (GalA) and 1,4-linked methyl galacturonate (MeGalA) residues with interspersed α-1,2 linked rhamnose within the carbohydrate backbone, the rhamnose residues carrying a primary branching of oligomers of 1,4-β-D-galactose residues, 1,5-α-L-arabinose residues, or combinations thereof, wherein the molar percent of the oligomers of 1,4-β-D-galactose residues and 1,5-α-L-arabinose residues is greater than 10% of the total carbohydrate molar content, wherein the 1,4-β-D-galactose, and 1,5-α-L-arabinose residues are present in a 2:1 to a 3:1 ratio and wherein the galactoarabino-rhamnogalacturonate has a degree of methoxylation from 33% to 66%; and b. a therapeutically effective amount of an immunotherapeutic agent or a vaccine directed against CTLA4, OX40, PD-1, PD-L or combinations thereof.

2. The composition of claim 1 wherein the 1,4-linked galacturonic acid and methyl galacturonate residues backbone represents between 55 to 85 molar percent of the total carbohydrate molar content, the branched heteropolymer of alternating α-1,2 linked rhamnose and α-1,4-linked GalA residues represents between 1 and 6 molar percent of the total carbohydrate molar content, the oligomer 1,4-β-D-galactose of the primary branching represents between 6 to 15 molar percent of the total carbohydrate molar content and the oligomer 1,5-α-L-arabinose of the primary branching represents between 2 to 8 molar percent of the total carbohydrate molar content, as characterized by gas chromatography/mass spectrometry.

3. The composition of claim 1 wherein the arabinogalacto-rhamnogalacturonan compound further comprises xylose, glucose, fucose residues or combination thereof.

4. The composition of claim 1 wherein the oligomer of 1,4-β-D-galactose residues, 1,5-α-L-arabinose residues or combinations thereof represents at least 8 molar percent of the total carbohydrate molar content.

5. The composition of claim 1, wherein the arabinogalacto-rhamnogalacturonan compound has an average molecular weight ranging from 2 kDa to 80 kDa.

6. The composition of claim 1, wherein the arabinogalacto-rhamnogalacturonan compound has an average molecular weight ranging from 20 kDa to 70 kDa.

7. The composition of claim 1, wherein the arabinogalacto-rhamnogalacturonan compound has an average molecular weight ranging from 5 kDa to 55 kDa.

8. The composition of claim 1, wherein the arabinogalacto-rhamnogalacturonan compound has a degree of methoxylation ranging from 40% to 70% of the maximum of 87%.

9. The composition of claim 1, wherein the arabinogalacto-rhamnogalacturonan compound has a methyl galacturonate plus galacturonic acid ratio to galactose ranging from 4:1 to 7:1.

10. The composition of claim 1, wherein the arabinogalacto-rhamnogalacturonan compound is capable of reducing expression of galectin-3 or of substantially decreasing secretion of galectin-3 when used to treat stressed LX2 immortalized human hepatic stellate cells producing galectin-3.

11. The composition of claim 1, further comprising an acceptable pharmaceutical carrier for use in therapeutic formulations.

12. The composition of claim 11 wherein the composition is formulated to be administered parenterally via an intravenous, subcutaneous, or oral route.

13. The composition of claim 1 for use in the treatment of cancer disorders in which galectins are at least in part involved in the pathogenesis.

* * * * *